United States Patent
Maeda

(10) Patent No.: US 12,020,433 B2
(45) Date of Patent: Jun. 25, 2024

(54) CELL EVALUATION DEVICE, OPERATION METHOD FOR CELL EVALUATION DEVICE, OPERATION PROGRAM FOR CELL EVALUATION DEVICE, AND CELL CULTURE SYSTEM

(71) Applicant: FUJIFILM Corporation, Tokyo (JP)

(72) Inventor: Kiyohiro Maeda, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 336 days.

(21) Appl. No.: 17/474,621

(22) Filed: Sep. 14, 2021

(65) Prior Publication Data
US 2021/0407089 A1 Dec. 30, 2021

Related U.S. Application Data

(63) Continuation of application No. PCT/JP2020/001263, filed on Jan. 16, 2020.

(30) Foreign Application Priority Data

Mar. 29, 2019 (JP) .................................. 2019-067743

(51) Int. Cl.
*G06T 7/00* (2017.01)
*C12M 1/34* (2006.01)
(Continued)

(52) U.S. Cl.
CPC ........... *G06T 7/0016* (2013.01); *C12M 41/46* (2013.01); *C12M 41/48* (2013.01); *C12M 41/14* (2013.01);
(Continued)

(58) Field of Classification Search
CPC ........ G06T 7/0016; G06T 2207/30024; C12M 41/46; C12M 41/48; C12M 41/14; C12N 5/0618
(Continued)

(56) References Cited

U.S. PATENT DOCUMENTS

| 8,792,703 B2 | 7/2014 | Nakano et al. |
| 2003/0103662 A1 | 6/2003 | Finkbeiner |

(Continued)

FOREIGN PATENT DOCUMENTS

| JP | 2005-514589 A | 5/2005 |
| JP | 2006-325427 A | 12/2006 |

(Continued)

OTHER PUBLICATIONS

Extended European Search Report for European Application No. 20783474.8, dated May 4, 2022.
(Continued)

*Primary Examiner* — Michael R Neff
(74) *Attorney, Agent, or Firm* — Birch, Stewart, Kolasch & Birch, LLP

(57) ABSTRACT

There is provided a cell evaluation device comprising an acquisition unit that acquires an image set of a plurality of cell images in which a plurality of cells having a protrusive structure are imaged in time series during culture; a reception unit that receives designation of a cell of interest which is a cell of interest to a user, the cell being at least one cell among the plurality of cells which are shown in one cell image of interest other than an oldest cell image in the image set; a specifying unit that captures a growth process of the protrusive structure based on the image set to specify a protrusive structure of interest, which is the protrusive structure extending from the cell of interest in the cell image of interest; and a display control unit that performs control to display the protrusive structure of interest in a display form different from that of other protrusive structures in the cell image of interest.

9 Claims, 22 Drawing Sheets

(51) Int. Cl.
　　　*C12M 1/36* 　　(2006.01)
　　　*C12M 1/00* 　　(2006.01)
　　　*C12N 5/079* 　　(2010.01)

(52) U.S. Cl.
　　　CPC .. *C12N 5/0618* (2013.01); *G06T 2207/30024* (2013.01)

(58) Field of Classification Search
　　　USPC ......................................................... 382/128
　　　See application file for complete search history.

(56) References Cited

U.S. PATENT DOCUMENTS

| | | | |
|---|---|---|---|
| 2009/0070089 A1 | 3/2009 | Kawato et al. | |
| 2011/0110942 A1* | 5/2011 | Kallop | A61P 25/18 530/389.1 |
| 2018/0053301 A1* | 2/2018 | Oshima | G06T 7/0016 |
| 2018/0268557 A1* | 9/2018 | Watanabe | G06T 7/246 |
| 2018/0276246 A1 | 9/2018 | Matsumoto | |

FOREIGN PATENT DOCUMENTS

| | | |
|---|---|---|
| JP | 2009-63509 A | 3/2009 |
| JP | 2012-200156 A | 10/2012 |
| JP | 2013-236564 A | 11/2013 |
| JP | 2017-117302 A | 6/2017 |
| JP | 2017-176020 A | 10/2017 |
| WO | WO 2007/069414 A1 | 6/2007 |

OTHER PUBLICATIONS

Fanti et al., "NeuronGrowth, a Software for Automatic Quantification of Neurite and Filopodial Dynamics from Time-Lapse Sequences of Digital Images," Developmental Neurobiology, vol. 71, No. 10, pp. 870-881, 12 pages total.

Fusco et al., "Computer vision profiling of neurite outgrowth dynamics reveals spatiotemporal modularity of Rho GTPase signaling," The Journal of Cell Biology, vol. 212, No. 1, 2016, pp. 91-111, 21 pages total.

Mbf Bioscience, "Webinar: Automatic neuron reconstruction/analysis with Neurolucida 360," YouTube, retrieved from the Internet, URL: https://www.youtube.com/watch?v =-oczrMQyrRA, Sep. 28, 2015, 2 pages total.

Japanese Office Action for corresponding Japanese Application No. 2021-511124, dated Jan. 10, 2023, with English translation.

Tsai et al., "Usiigaci: Instance-aware cell tracking in stain-free phase contrast microscopy enabled by machine learning," SoftwareX, vol. 9, 2019, pp. 230-237.

Japanese Office Action for corresponding Japanese Application No. 2021-511124, dated Jun. 6, 2023, with English translation.

International Preliminary Report on Patentability and English Translation of the Written Opinion of the International Searching Authority for International Application No. PCT/JP2020/001263, dated Oct. 14, 2021.

International Search Report for International Application No. PCT/JP2020/001263, dated Mar. 24, 2020, with English translation.

Japanese Office Action for corresponding Japanese Application No. 2021-511124, dated Jul. 12, 2022, with English translation.

* cited by examiner

CELL EVALUATION DEVICE, OPERATION METHOD FOR CELL EVALUATION DEVICE, OPERATION PROGRAM FOR CELL EVALUATION DEVICE, AND CELL CULTURE SYSTEM

CROSS-REFERENCE TO RELATED APPLICATIONS

This application is a continuation application of International Application No. PCT/JP2020/001263 filed on Jan. 16, 2020, the disclosure of which is incorporated herein by reference in its entirety. Further, this application claims priority from Japanese Patent Application No. 2019-067743 filed on Mar. 29, 2019, the disclosure of which is incorporated herein by reference in its entirety.

BACKGROUND

1. Technical Field

The techniques of the present disclosure relate to a cell evaluation device, an operation method for a cell evaluation device, an operation program for a cell evaluation device, and a cell culture system.

2. Description of the Related Art

Some cells have a protrusive structure. For example, a nerve cell has a cell body having a nucleus, an axon, and dendrites extending from the cell body, and the axon and the dendrites correspond to the protrusive structure.

The protrusive structure extends in length and branches in some places during the cell growth process. For this reason, in a case of evaluating cells having such a protrusive structure, the length of the protrusive structure, the number of branching times, and the like are often used as evaluation indicators. For example, JP2009-063509A describes a technique for determining the lengths of an axon and dendrites, the number of branching times, and the like by analyzing a cell image in which nerve cells are shown.

SUMMARY

However, in cell culture, since a plurality of cells are densely seeded, it is inevitable that protrusive structures extending from the cell bodies of different cells complicatedly intersect with each other. Accordingly, in the cell image in which cells under culturing are shown, the protrusive structure extending from the cell body of the cell of interest to a user (hereinafter, referred to as the cell of interest) intersects with a protrusive structure extending from a cell body of another cell, and thus, in many cases, it is unclear which protrusive structure extends from the cell body of the cell of interest. As a result, even in a case where a user desires to evaluate the cells of interest individually, it is difficult to carry out such an evaluation.

An object of the technique of the present disclosure is to provide a cell evaluation device with which cells of interest to a user can be individually evaluated, an operation method for a cell evaluation device, an operation program for a cell evaluation device, and a cell culture system.

For achieving the above object, the cell evaluation device of the present disclosure includes an acquisition unit that acquires an image set of a plurality of cell images in which a plurality of cells having a protrusive structure are imaged in time series during culture; a reception unit that receives designation of a cell of interest which is a cell of interest to a user, the cell being at least one cell among the plurality of cells which are shown in one cell image of interest other than the oldest cell image in the image set; a specifying unit that captures a growth process of the protrusive structure based on the image set to specify a protrusive structure of interest, which is the protrusive structure extending from the cell of interest in the cell image of interest; and a display control unit that performs control to display the protrusive structure of interest in a display form different from that of other protrusive structures in the cell image of interest.

It is preferable that the specifying unit generates a difference image of two cell images which are chronologically continuous in the image set and determines the connectivity between the protrusive structure which is shown in the difference image and the protrusive structure which is shown in an older cell image of the two cell images preceding and following in time to specify the protrusive structure of interest.

It is preferable to include a calculation unit that calculates at least any one of a length, a thickness, an area, or the number of branching times of the protrusive structure of interest; and an output control unit that performs control to output a calculation result of the calculation unit.

It is preferable that the cell is a nerve cell, the protrusive structure is a dendrite, and the calculation unit calculates the number of spines formed on the dendrite.

It is preferable that the calculation unit calculates at least one of the number of spines per unit length of the dendrite or the number of the spines per unit area of the dendrite.

It is preferable that the cell image of interest is the latest cell image in the image set.

The operation method for a cell evaluation device of the present disclosure an acquisition step of acquiring an image set of a plurality of cell images in which a plurality of cells having a protrusive structure are imaged in time series during culture; a reception step of receiving a designation of a cell of interest which is a cell of interest to a user, the cell being at least one cell among the plurality of cells which are shown in one cell image of interest other than an oldest cell image in the image set; a specification step of capturing a growth process of the protrusive structure based on the image set to specify a protrusive structure of interest, which is the protrusive structure extending from the cell of interest in the cell image of interest; and a display control step of performing control to display the protrusive structure of interest in a display form different from that of other protrusive structures in the cell image of interest.

The operation program for a cell evaluation device of the present disclosure causes a computer to function as an acquisition unit that acquires an image set of a plurality of cell images in which a plurality of cells having a protrusive structure are imaged in time series during culture; a reception unit that receives designation of a cell of interest which is a cell of interest to a user, the cell being at least one cell among the plurality of cells which are shown in one cell image of interest other than an oldest cell image in the image set; a specifying unit that captures a growth process of the protrusive structure based on the image set to specify a protrusive structure of interest, which is the protrusive structure extending from the cell of interest in the cell image of interest; and a display control unit that performs control to display the protrusive structure of interest in a display form different from that of other protrusive structures in the cell image of interest.

The cell culture system of the present disclosure includes the cell evaluation device according to any one of claims 1 to 6; an incubator that accommodates a culture instrument of a cell; and an imaging device that takes an image of the cell in a state where the culture instrument is accommodated in the incubator.

According to the technique of the present disclosure, it is possible to provide a cell evaluation device with which cells of interest to a user can be individually evaluated, an operation method for a cell evaluation device, an operation program for a cell evaluation device, and a cell culture system.

BRIEF DESCRIPTION OF THE DRAWINGS

Exemplary embodiments according to the technique of the present disclosure will be described in detail based on the following figures, wherein:

FIG. 1 is a diagram illustrating a cell evaluation device and the like;

DETAILED DESCRIPTION

First Embodiment

Figure 1:
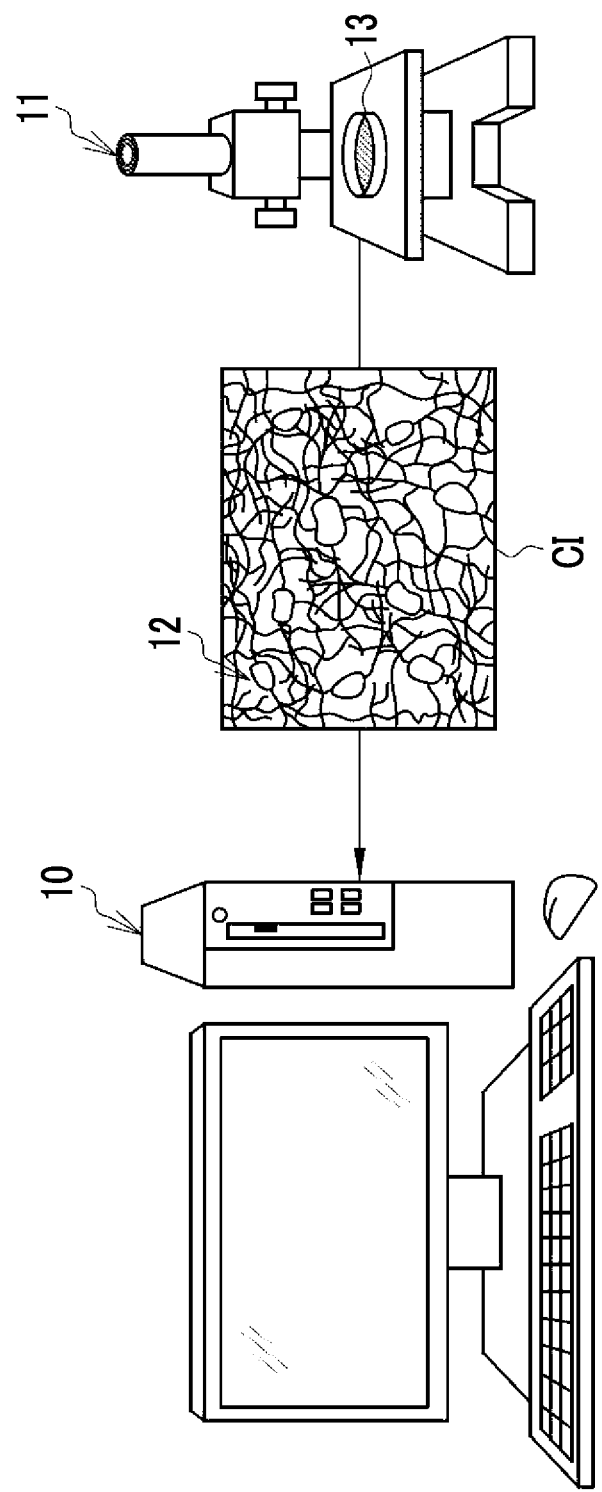

In FIG. 1, a cell evaluation device 10 is, for example, a device that evaluates a cell which has been induced to differentiate from an induced pluripotent stem (iPS) cell and is, for example, a desktop personal computer. A cell image CI in which cells under culture are imaged is input to the cell evaluation device 10. The cell image CI is taken by an operator with an imaging device 11 such as a digital phase-contrast microscope. The operator is an example of a "user" according to the technique of the present disclosure. In addition, a reference numeral 13 indicates a culture instrument such as a petri dish.

Figure 2:
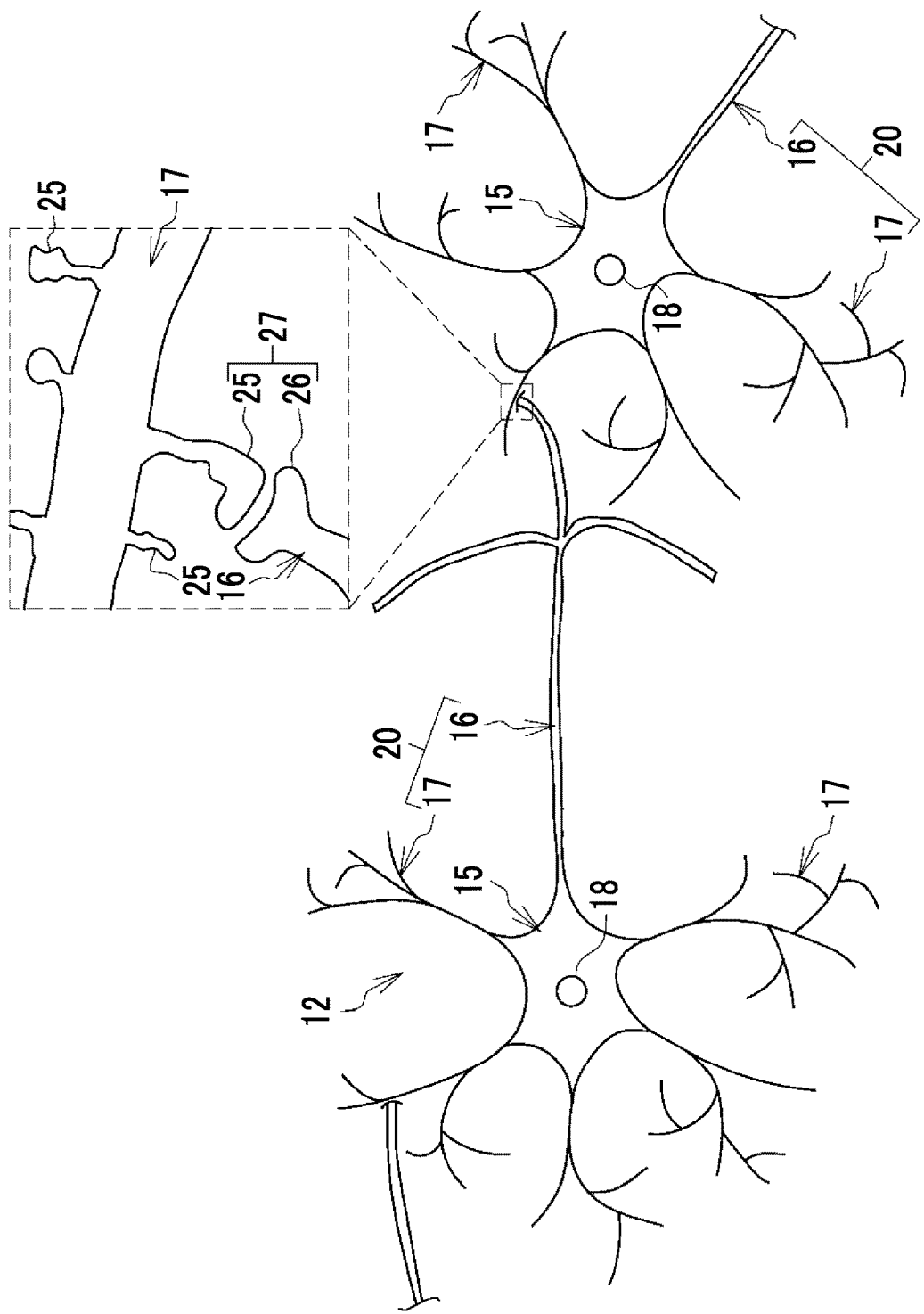
FIG. 2 is a diagram illustrating a structure of nerve cells.

In the present example, a cell evaluated by the cell evaluation device 10 is a nerve cell 12. As illustrated in FIG. 2, the nerve cell 12 has a cell body 15, an axon 16, and a dendrite 17. The cell body 15 has a nucleus 18 and forms the center of the nerve cell 12. The axon 16 extends from the cell body 15 and plays a role in outputting a neurotransmitter to another nerve cell 12. Basically, only one axon 16 extends from one cell body 15; however, a branch called an axon collateral is formed during the growth process. The dendrite 17 also extends from the cell body 15. However, contrary to the axon 16, the dendrite 17 plays a role in receiving a neurotransmitter from another nerve cell 12. Unlike the axon 16, a plurality of dendrites 17 may extend from one cell body 15. In addition, the dendrite 17 spreads while literally branching into a dendritic shape during the growth process.

Each of these axon 16 and dendrite 17 is an example of the "protrusive structure" according to the technique of the present disclosure. Hereinafter, the axon 16 and the dendrite 17 are collectively written as a protrusive structure 20.

As illustrated inside the broken line, a plurality of spines 25, which are spinous protrusions, are formed on the surface of the dendrite 17. A part of the plurality of spines 25 and a presynaptic terminal 26 of another nerve cell 12 constitute a synapse 27 for giving and taking a neurotransmitter. The presynaptic terminal 26 is a bulged part at the distal end of the axon 16.

Figure 3:
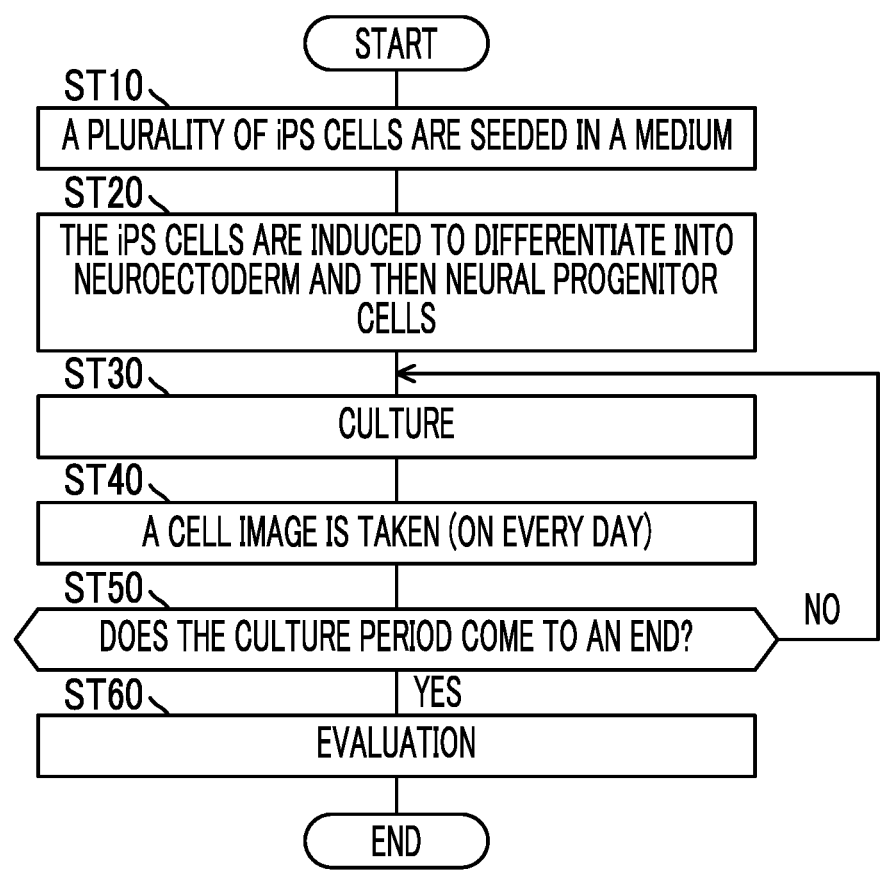
FIG. 3 is a flowchart illustrating a flow of culturing nerve cells.

FIG. 3 is a flowchart illustrating the flow of culturing the nerve cell 12. First, an operator seeds a plurality of iPS cells in a medium of a culture instrument 13 (a step ST10). Then, the iPS cells are induced to differentiate into neuroectoderm and then neural progenitor cells in order (a step ST20). As a result, the culture of the nerve cell 12 is started (a step ST30).

During culture, the operator takes the cell image CI using the imaging device 11 at regular imaging intervals, for example, every day (a step ST40). At this time, the operator sets the culture instrument 13 in the imaging device 11 so that the imaging position is the same every time, and then takes the cell image CI. Taking the cell image CI is continued until the preset culture period comes to an end (YES in a step ST50). After the end of the culture period, the operator evaluates the nerve cell 12 using the cell evaluation device 10 (a step ST60).

Figure 4:
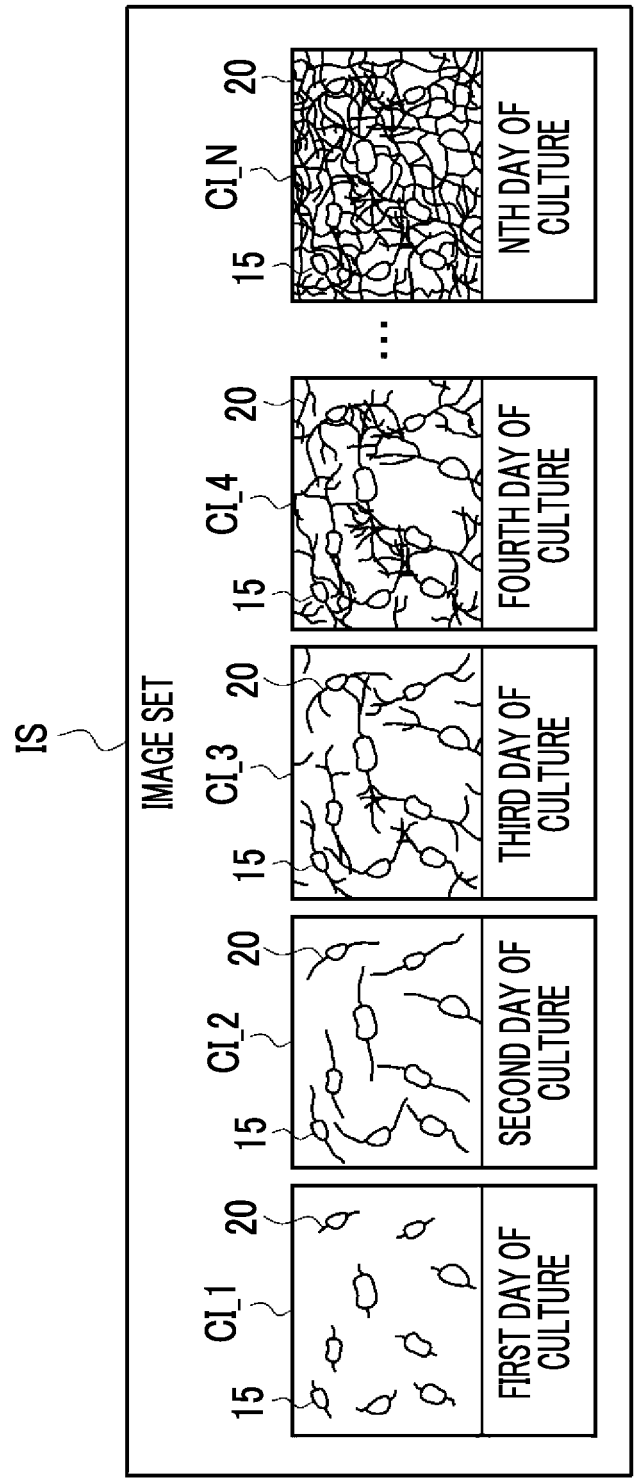
FIG. 4 is a diagram illustrating an image set.

The cell evaluation device 10 carries out evaluation with reference to an image set IS illustrated in FIG. 4. The image set IS is a collection of a plurality of cell images CI in which the nerve cells 12 are imaged in time series during culture. In the case of the present example, since the cell image CI is taken every day, the image set IS is composed of a cell image CI_1 on the first day of culture (the start day of culture), a cell image CI_2 on the second day of culture, a cell image CI_3 on the third day of culture, a cell image CI_4 on the fourth day of culture, . . . , and a cell image CI_N on the Nth day of culture (the last day of culture). The first day of culture is the day when the iPS cells are induced to differentiate into neural progenitor cells.

In the cell image CI_1 on the first day of culture, the cell bodies 15 are mainly shown, and the protrusive structures 20 are rarely seen. However, the protrusive structures 20 extend or branch as days pass by the second day of culture, the third day of culture, and so on. Then, on the Nth day of culture, it is at first glance indistinguishable which protrusive structure 20 extends from which cell body 15 of the nerve cell 12.

Figure 5:
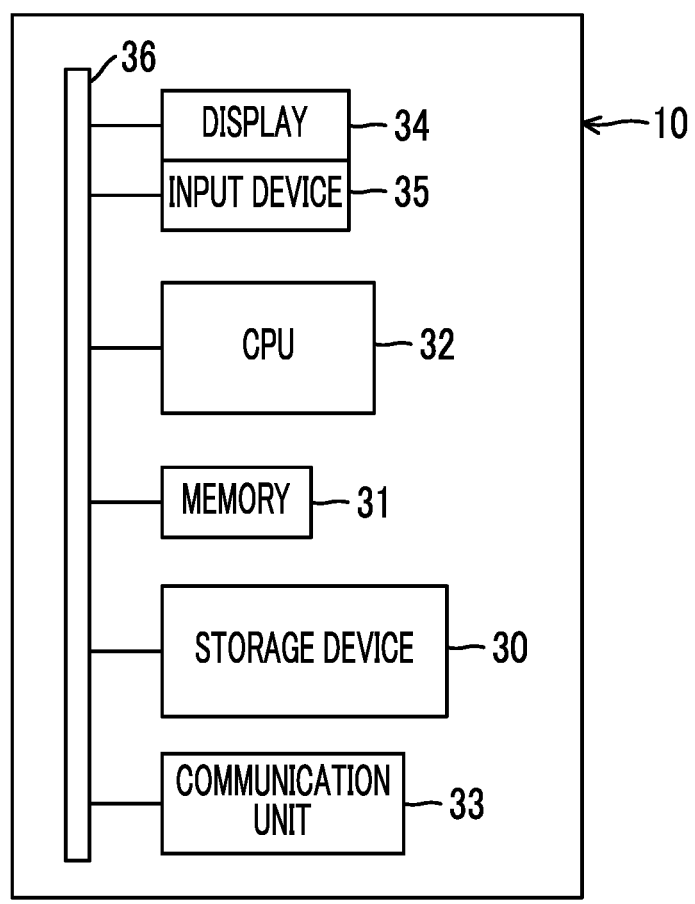
FIG. 5 is a block diagram illustrating a computer that constitutes the cell evaluation device.

In FIG. 5, a computer constituting the cell evaluation device 10 includes a storage device 30, a memory 31, a central processing unit (CPU) 32, a communication unit 33, a display 34, and an input device 35. These components are connected to each other through a busline 36.

The storage device 30 is a hard disk drive that is built in the computer that constitutes the cell evaluation device 10 or is connected to the computer through a cable or a network. Alternatively, the storage device 30 is a disk array in which a plurality of hard disk drives are connectively mounted. The storage device 30 stores a control program such as an operating system, various application programs, various types of data associated with these programs, and the like.

The memory 31 is a work memory that is used in a case where the CPU 32 executes processing. The CPU 32 loads the program stored in the storage device 30 into the memory 31 and executes processing according to the program, thereby comprehensively controlling each of the units of the computer.

The communication unit 33 is a network interface that controls the transmission of various information via a network such as a local area network (LAN) or a wide area network (WAN). The display 34 displays various screens. The computer that constitutes the cell evaluation device 10 receives an input of an operation command from the input device 35, through the various screens. The input device 35 is a keyboard, a mouse, a touch panel, or the like.

Figure 6:
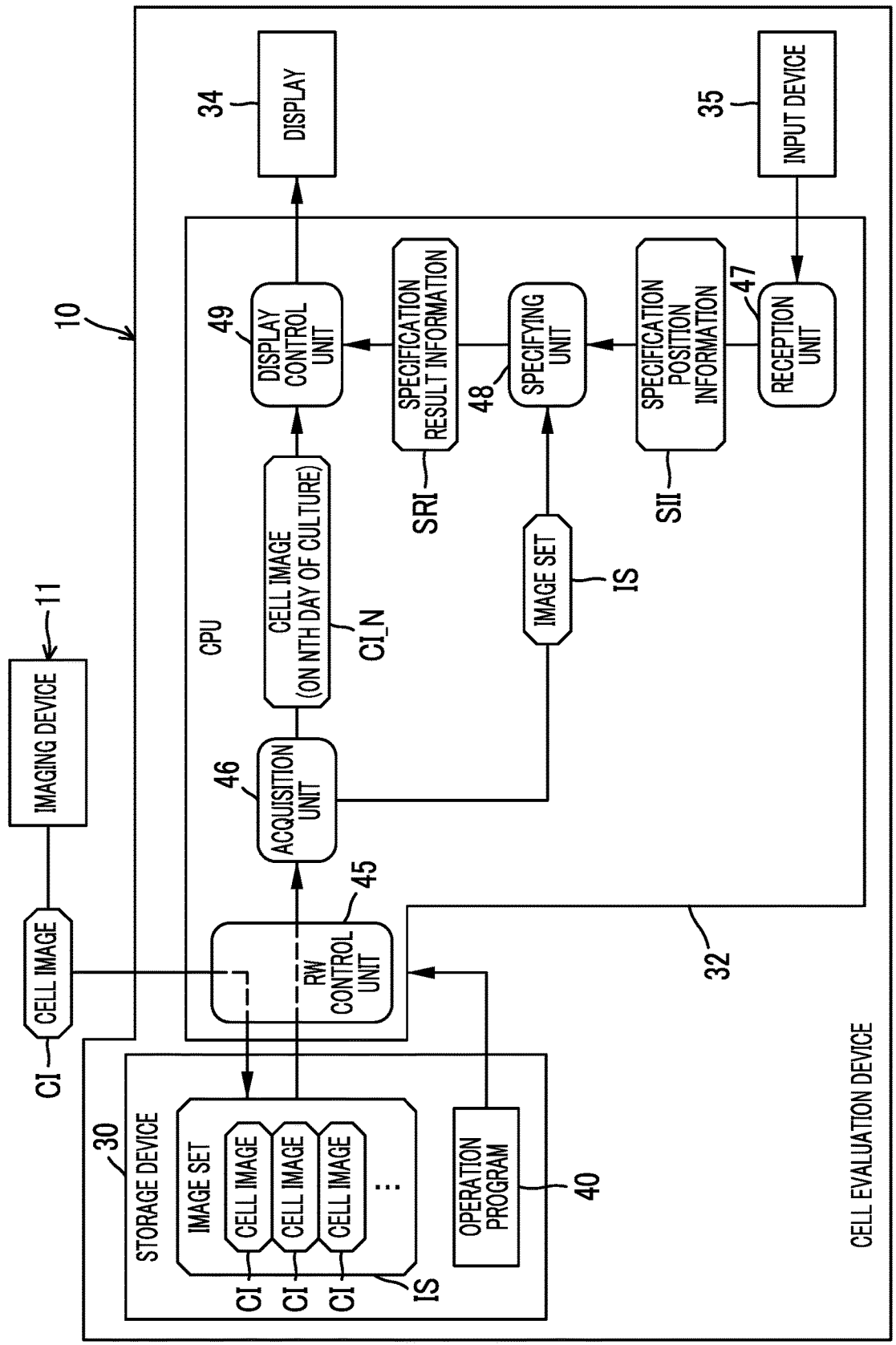
FIG. 6 is a block diagram illustrating a processing unit of a CPU of the cell evaluation device.

In FIG. 6, an operation program 40 is stored in the storage device 30 of the cell evaluation device 10. The operation program 40 is an application program for making a computer function as the cell evaluation device 10. That is, the operation program 40 is an example of the "operation program for the cell evaluation device" according to the technique of the present disclosure.

In a case where the operation program 40 is activated, the CPU 32 of the computer constituting the cell evaluation device 10 cooperates with the memory 31 and the like to function as a read and write (hereinafter, abbreviated as RW) control unit 45, an acquisition unit 46, a reception unit 47, a specifying unit 48, and a display control unit 49.

The RW control unit 45 controls the reading-out of various data in the storage device 30 and the storage of various data in the storage device 30. The RW control unit 45 stores the cell image CI from the imaging device 11 in the storage device 30. In a case where the storage of the cell image CI is continued from the first day of culture to the Nth day of culture, the image set IS illustrated in FIG. 4 is stored in the storage device 30. In addition, the RW control unit 45 reads out the image set IS from the storage device 30 and outputs the read-out image set IS to the acquisition unit 46.

The acquisition unit 46 acquires the image set IS from the RW control unit 45. The acquisition unit 46 outputs the image set IS to the specifying unit 48 and outputs the cell image CI_N on the Nth day of culture in the image set IS to the display control unit 49. The cell image CI_N on the Nth day of culture is an example of the "latest cell image" according to the technique of the present disclosure.

The reception unit 47 receives a designation of a cell of interest 12I (see FIG. 7) which is a nerve cell 12 of interest to an operator, the cell being at least one nerve cell 12 among the plurality of nerve cells 12 which are shown in the cell image CI_N on the Nth day of culture. The reception unit 47 creates a designation position information SII that indicates the position of the cell of interest 12I in the cell image CI_N on the Nth day of culture. The designation position information SII is, for example, the XY coordinates of the pixel corresponding to the center of the cell body 151 (see FIG. 7) of the cell of interest 12I. The reception unit 47 outputs the designation position information SII to the specifying unit 48.

The specifying unit 48 captures the growth process of the protrusive structure 20 based on the image set IS from the acquisition unit 46. Based on the result of capturing the growth process of the protrusive structure 20 and the designation position information SII from the reception unit 47, the specifying unit 48 specifies the protrusive structure of interest 20I (see FIG. 10 and the like) which is the protrusive structure 20 of the cell of interest 12I in the cell image CI_N on the Nth day of culture. The specifying unit 48 creates a specification result information SRI that indicates the specification result of the protrusive structure of interest 20I. The specification result information SRI is, for example, the XY coordinates of the pixel corresponding to the protrusive structure of interest 20I of the cell image CI_N on the Nth day of culture. The specifying unit 48 outputs the specification result information SRI to the display control unit 49.

The display control unit 49 performs control to display various screens on the display 34. For example, the display control unit 49 performs control to display a designation screen for a cell of interest 60 (see FIG. 7) for designating the cell of interest 12I or a specification result display screen 70 (see FIG. 14) or the like, which shows the specification result of the protrusive structure of interest 20I by the specifying unit 48, on the display 34.

Figure 7:
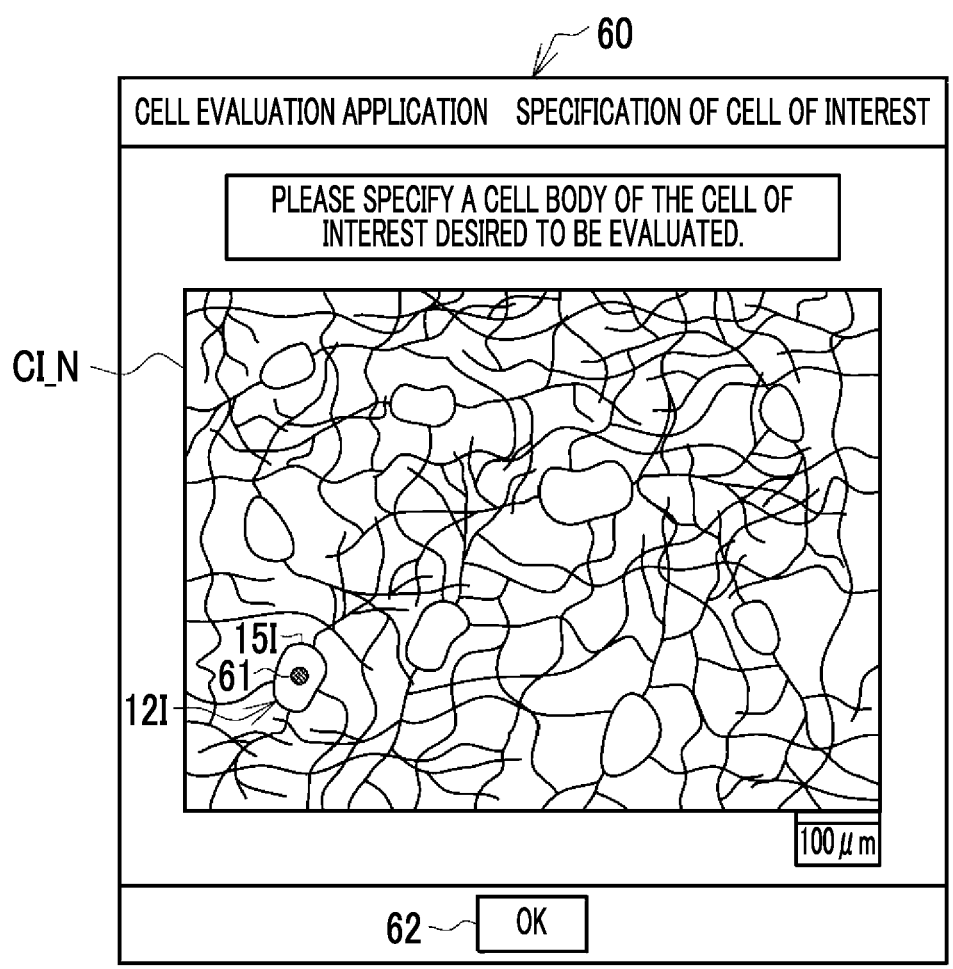
FIG. 7 is a diagram illustrating a designation screen for a cell of interest.

As illustrated in FIG. 7, under the control of the display control unit 49, the cell image CI_N on the Nth day of culture is displayed on the designation screen for a cell of interest 60, which is displayed on the display 34. The operator inputs a dot-shaped round marker 61 in the cell body 151 of the cell of interest 12I. After inputting the marker 61, the operator selects an OK button 62. In a case where the OK button 62 is selected, the reception unit 47 receives the designation that the nerve cell 12 in which the marker 61 is input in the cell body 151 is set as the cell of interest 12I. That is, the cell image CI_N on the Nth day of culture is an example of the "cell image of interest" according to the technique of the present disclosure.

Figure 8:
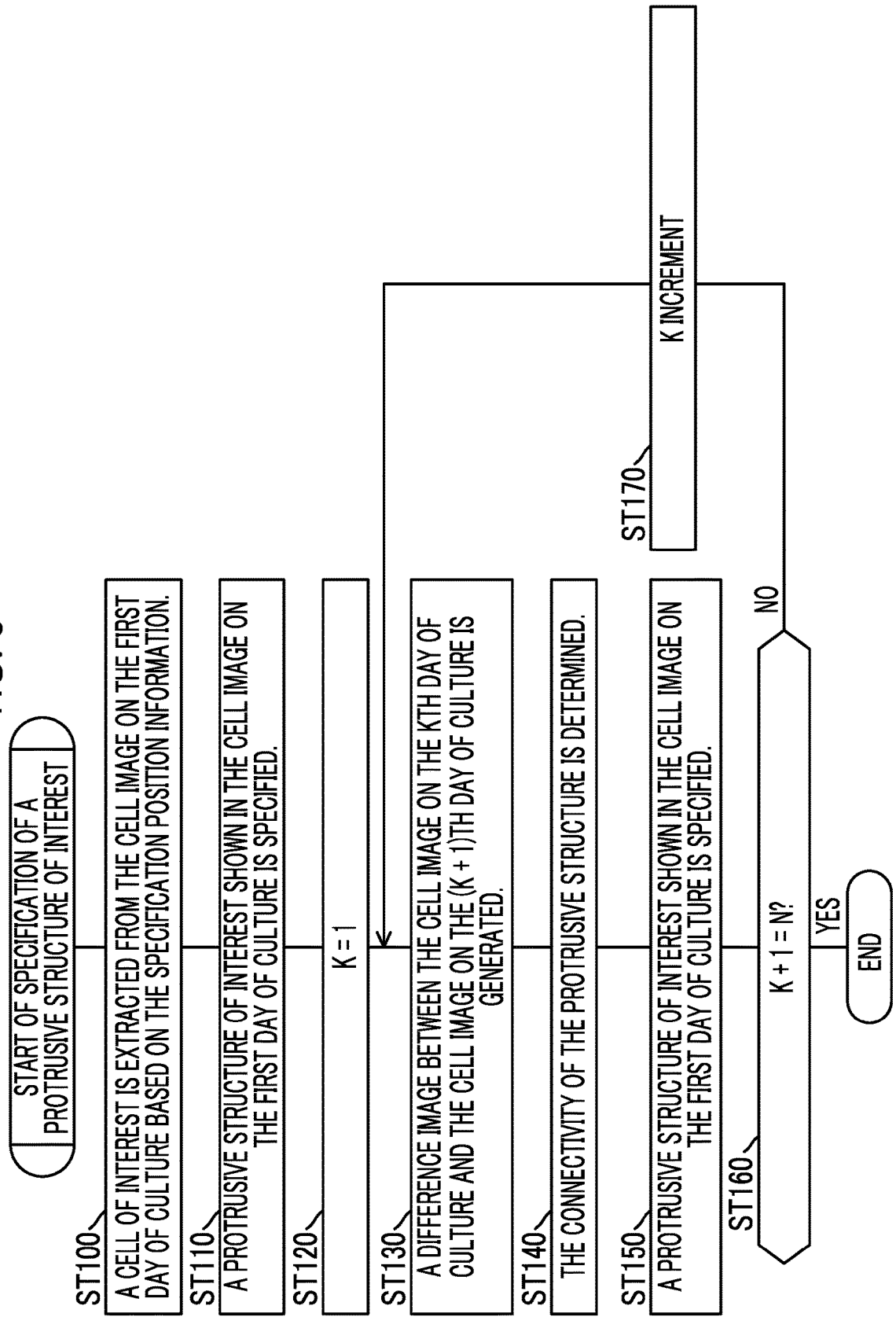
FIG. 8 is a flowchart illustrating a flow of processing of specifying a protrusive structure of interest in a specifying unit.

FIG. 8 is a flowchart illustrating a flow of processing of specifying a protrusive structure of interest 20I in a specifying unit 48. First, the specifying unit 48 extracts the cell of interest 12I of the cell image CI_1 based on the designation position information SII (a step ST100).

The specifying unit 48 specifies a protrusive structure of interest 20I_1 (see FIG. 10) extending from the cell of interest 12I that has been extracted in the step ST100 from the cell image CI_1 on the first day of culture (a step ST110).

The specifying unit 48 generates a difference image DI_K, K+1 between a cell image CI_K on the Kth day of culture and a cell image CI_K+1 on the (K+1)th day of culture (a step ST130). Then, the connectivity between a protrusive structure 20_K, K+1 which is shown in the difference image DI_K, K+1 and a protrusive structure of interest 20I_K which is shown in the cell image CI_K on the Kth day of culture is determined (a step ST140). The specifying unit 48 specifies a protrusive structure of interest 20I_K+1 which is shown in the cell image CI_K+1 on the (K+1)th day of culture based on the determination result of the connectivity in the step ST140 (a step ST150).

More specifically, first, the specifying unit 48 carries out processing of the step ST130, the step ST140, and the step ST150 with K=1 (a step ST120). Then, the specifying unit 48 increments K (NO in a step ST160, and a step ST170) until K+1=N, and repeats the processing of the step ST130, the step ST140, and step the ST150. It is noted that the cell image CI_K on the Kth day and the cell image CI_K+1 on the (K+1)th day are examples of the "two cell images which are chronologically continuous" according to the technique of the present disclosure. In addition, the cell image CI_K on the Kth day is an example of the "older cell image of the two cell images which are chronologically continuous" according to the technique of the present disclosure.

Figure 9:
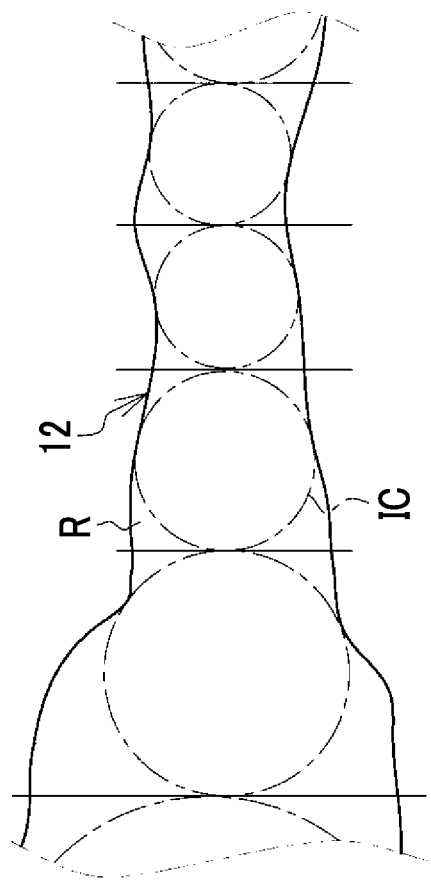
FIG. 9 is a diagram illustrating an outline of a method of extracting the protrusive structure.

The extraction of the protrusive structure of interest 20I_1, which is represented in the step ST110 of FIG. 8, is carried out, for example, by using the technique described in JP2009-063509A. In the technique described in JP2009-063509A, the outline of which is illustrated in FIG. 9, first, the cell image CI is subjected to the binarization processing, thereby being divided into a region constituting the nerve cell 12 and a region not constituting the nerve cell 12. Then, inscribed circles IC are provided so that they are not overlapped in the region constituting the nerve cell 12. Next, the region constituting the nerve cell 12 is divided into a plurality of small regions R including each of the inscribed circles IC. Subsequently, for each small region R, feature quantities such as the center point of the inscribed circle IC, the radius of the inscribed circle IC, and the average value of the pixel values are calculated. According to the center point of the inscribed circle IC, the shape of the nerve cell 12 can be traced almost accurately. The specifying unit 48 specifies, for example, a small region R in which the radius of the inscribed circle IC is equal to or shorter than a threshold value as the protrusive structure of interest 20I_1. The method of extracting the protrusive structure of interest 20I_1 is not limited to the method described in JP2009-063509A.

Figure 10:
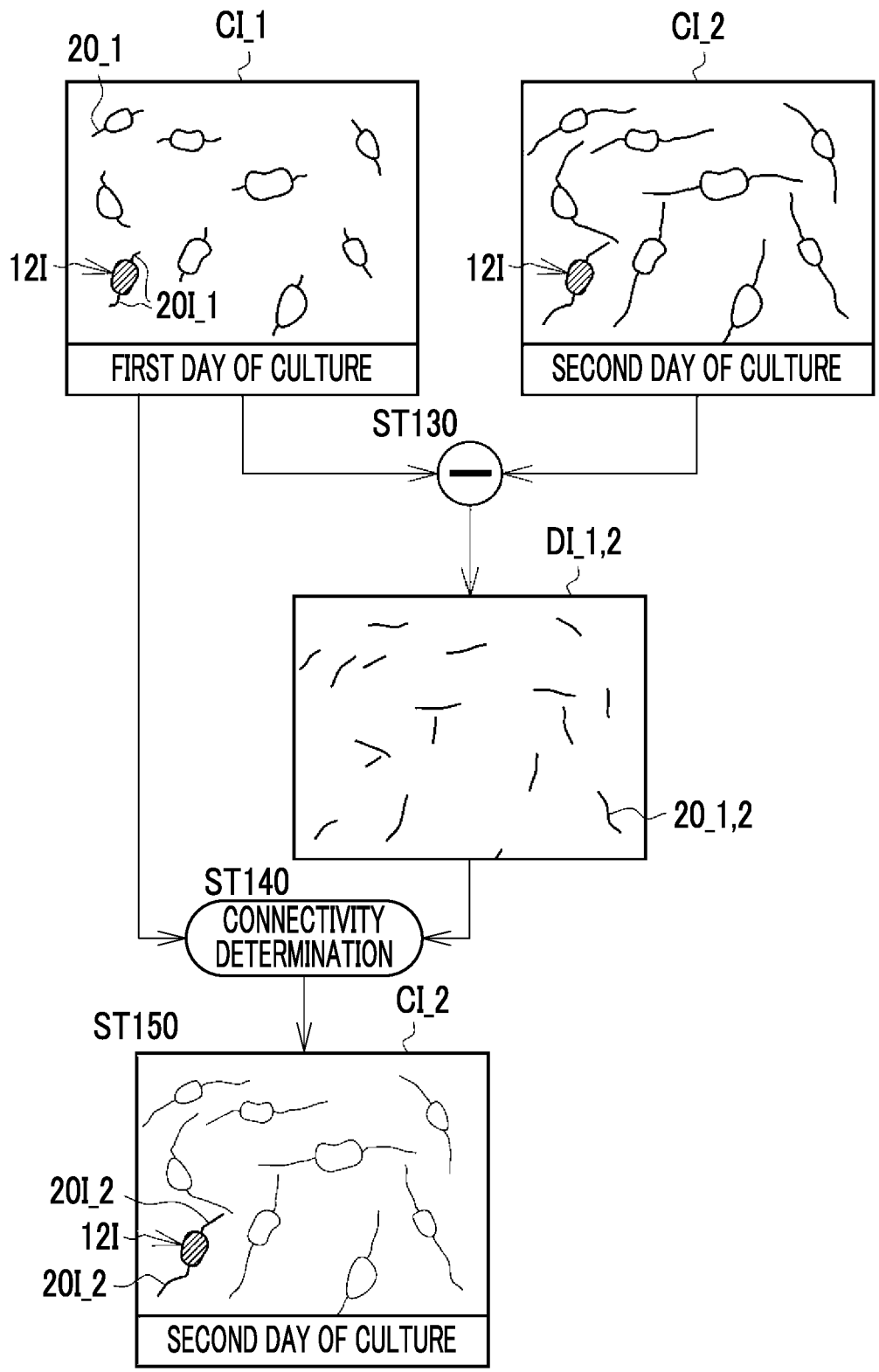
FIG. 10 is a diagram illustrating the processing of a step ST130, a step ST140, and a step ST150 in FIG. 8 in a case of K=1.
Figure 11:
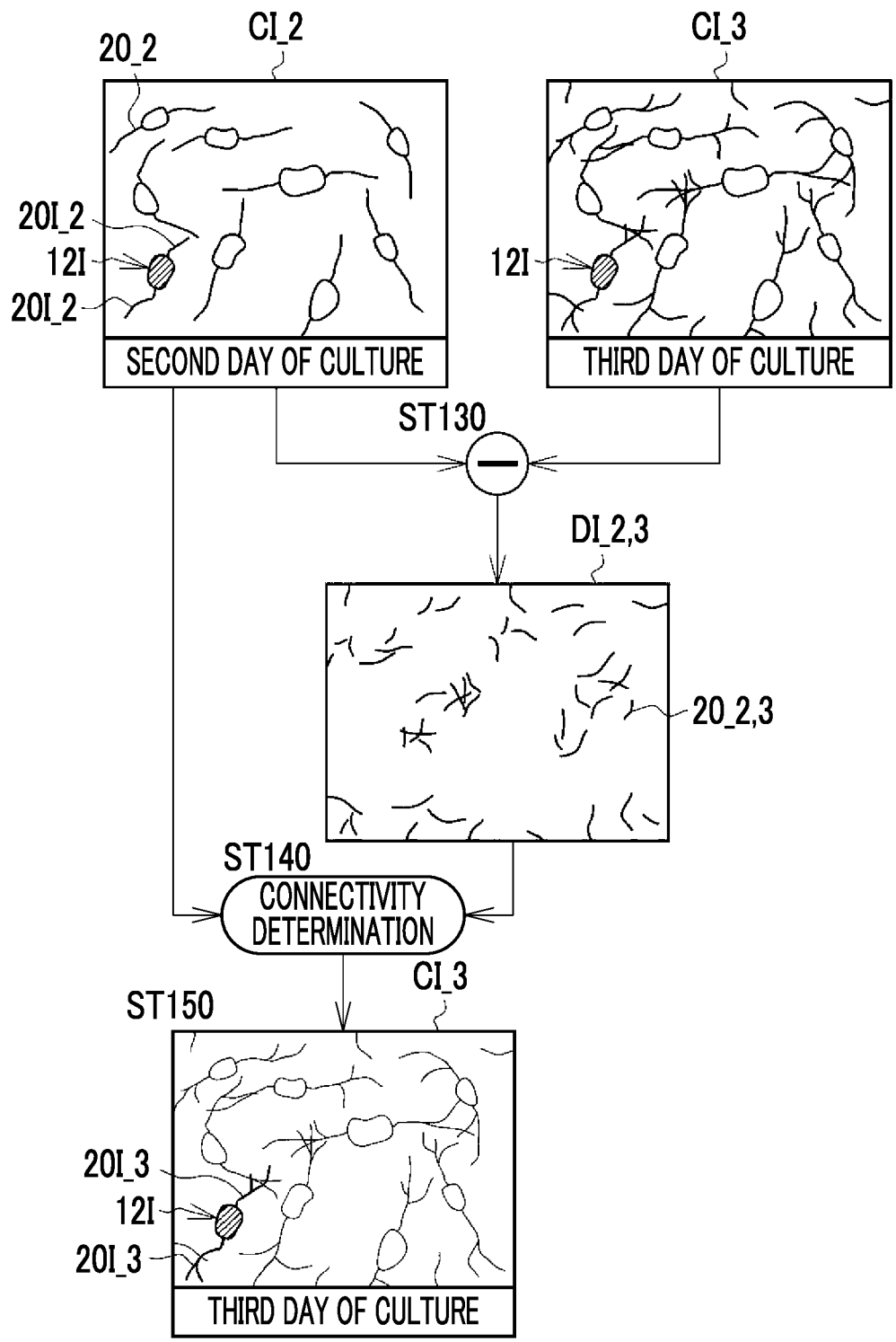
FIG. 11 is a diagram illustrating the processing of a step ST130, a step ST140, and a step ST150 in FIG. 8 in a case of K=2.
Figure 12:
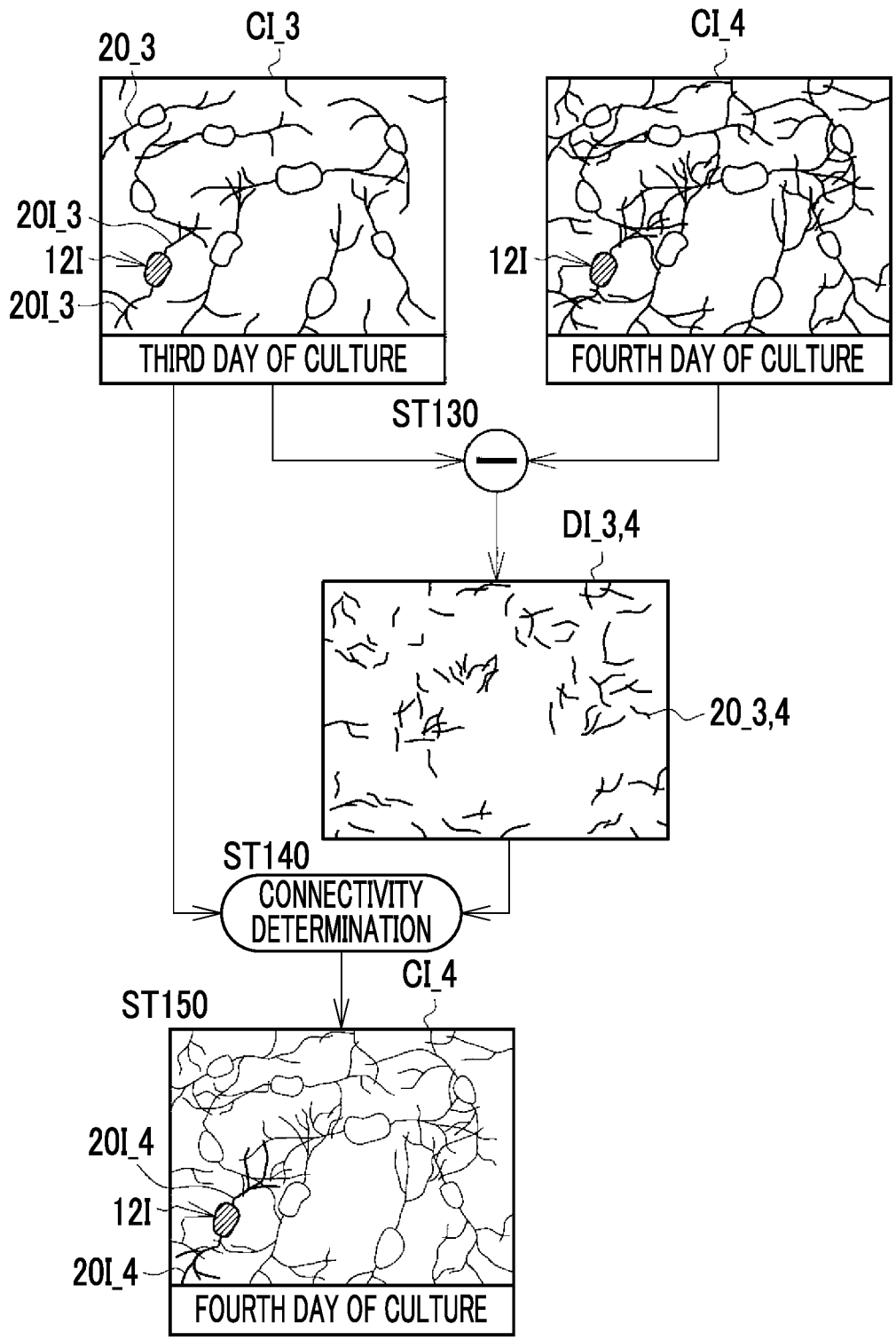
FIG. 12 is a diagram illustrating the processing of a step ST130, a step ST140, and a step ST150 in FIG. 8 in a case of K=3.

FIG. 10 to FIG. 12 are diagrams illustrating the processing of a step ST130, a step ST140, and a step ST150 in FIG. 8. A case of K=1 is illustrated in FIG. 10, a case of K=2 is illustrated in FIG. 11, and a case of K=3 is illustrated in FIG. 12.

As illustrated in FIG. 10, the specifying unit 48 generates a difference image DI_1, 2 between the cell image CI_1 on the first day of culture and the cell image CI_2 on the second day of culture. Then, the connectivity between a protrusive structure 20_1, 2 which is shown in the difference image DI_1, 2 and a protrusive structure of interest 20I_1 which is shown in the cell image CI_1 on the first day of culture is determined. Based on the determination result of this connectivity, the specifying unit 48 specifies the protrusive structure of interest 20I_2 which is shown in the cell image CI_2 on the second day of culture.

In the same manner, as illustrated in FIG. 11, the specifying unit 48 generates a difference image DI_2, 3 between the cell image CI_2 on the second day of culture and the cell image CI_3 on the third day of culture. Then, the connectivity between a protrusive structure 20_2, 3 which is shown in the difference image DI_2, 3 and a protrusive structure of interest 20I_2 which is shown in the cell image CI_2 on the second day of culture is determined. Based on the determination result of this connectivity, the specifying unit 48 specifies the protrusive structure of interest 20I_3 which is shown in the cell image CI_3 on the third day of culture.

Further, as illustrated in FIG. 12, the specifying unit 48 generates a difference image DI_3, 4 between the cell image CI_3 on the third day of culture and the cell image CI_4 on the fourth day of culture. Then, the connectivity between a protrusive structure 20_3, 4 which is shown in the difference image DI_3, 4 and a protrusive structure of interest 20I_3 which is shown in the cell image CI_3 on the third day of culture is determined. Based on the determination result of this connectivity, the specifying unit 48 specifies the protrusive structure of interest 20I_4 which is shown in the cell image CI_4 on the fourth day of culture. By repeating such processing until K+1=N is satisfied, the specifying unit 48 finally specifies the protrusive structure of interest 20I_N which is shown in the cell image CI_N on the Nth day of culture.

Figure 13:
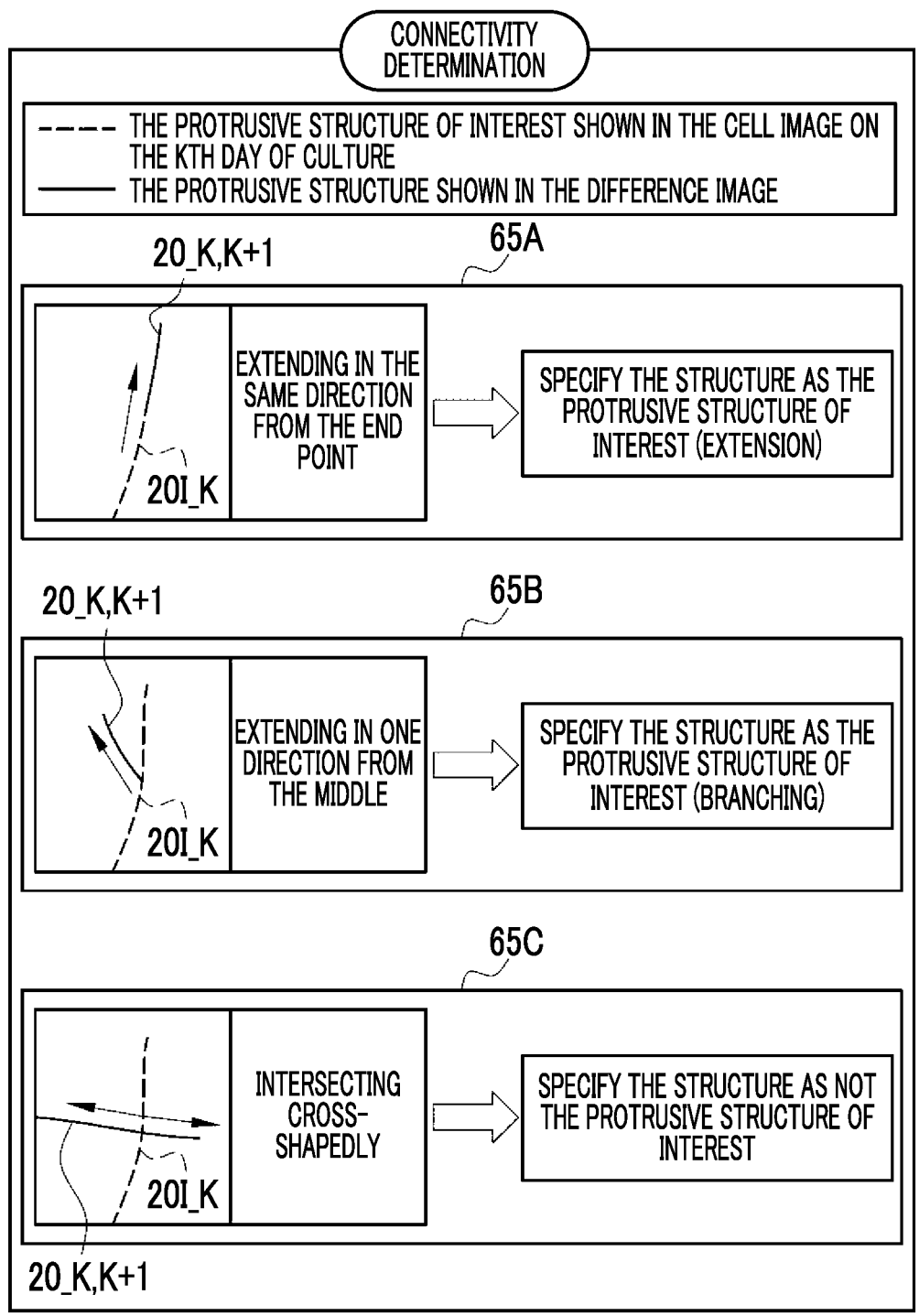
FIG. 13 is a diagram illustrating regulations for determining the connectivity of the protrusive structure.

The determination of the connectivity in the step ST140 is carried out, for example, according to a first regulation 65A, a second regulation 65B, and a third regulation 65C, which are illustrated in FIG. 13. The content of the first regulation 65A is that in a case where the protrusive structure 20_K, K+1 which is shown in the difference image DI_K, K+1, where the protrusive structure 20_K, K+1 is indicated by the solid line, extends in the same direction from the end point of the protrusive structure of interest 20I_K which is shown in the cell image CI_K on the Kth day, where the protrusive structure of interest 20I_K is indicated by the broken line, it is determined that the protrusive structure of interest 20I_K has extended to be the protrusive structure 20_K, K+1. The content of the second regulation 65B is that in a case where the protrusive structure 20_K, K+1 extends in one direction from the middle of the protrusive structure of interest 20I_K, it is determined that the protrusive structure of interest 20I_K has branched to be the protrusive structure 20_K, K+1.

On the other hand, the content of the third regulation 65C is that in a case where the protrusive structure 20_K, K+1 cross-shapedly intersect with the protrusive structure of interest 20I_K, it is determined that the protrusive structure 20_K, K+1 is not the protrusive structure of interest 20I_K.

The "same direction" of the first regulation 65A indicates, for example, a case where an angle formed by the protrusive structure of interest 20I_K and the protrusive structure 20_K, K+1, where the protrusive structures are linearly approximated, is within a range of 160° to 200°. In a case where the angle is 180°, the protrusive structure of interest 20I_K and the protrusive structure 20_K, K+1 are linearly connected.

It is also conceivable that the protrusive structure 20 is interrupted in some places due to noise. For this reason, in the first regulation 65A, it may be determined that the protrusive structure of interest 20I_K has extended in the case where the protrusive structure 20_K, K+1 is present at a distance separated within a threshold value from the end point of the protrusive structure of interest 20I_K and extends in the same direction as the protrusive structure of interest 20I_K. Similarly, in the second regulation 65B, it may be determined that the protrusive structure of interest 20I_K has branched in the case where the protrusive structure 20_K, K+1 is present at a distance separated within a threshold value from the middle of the protrusive structure of interest 20I_K and extends in one direction. The threshold value is set to, for example, 10 μm in terms of actual size.

Figure 14:
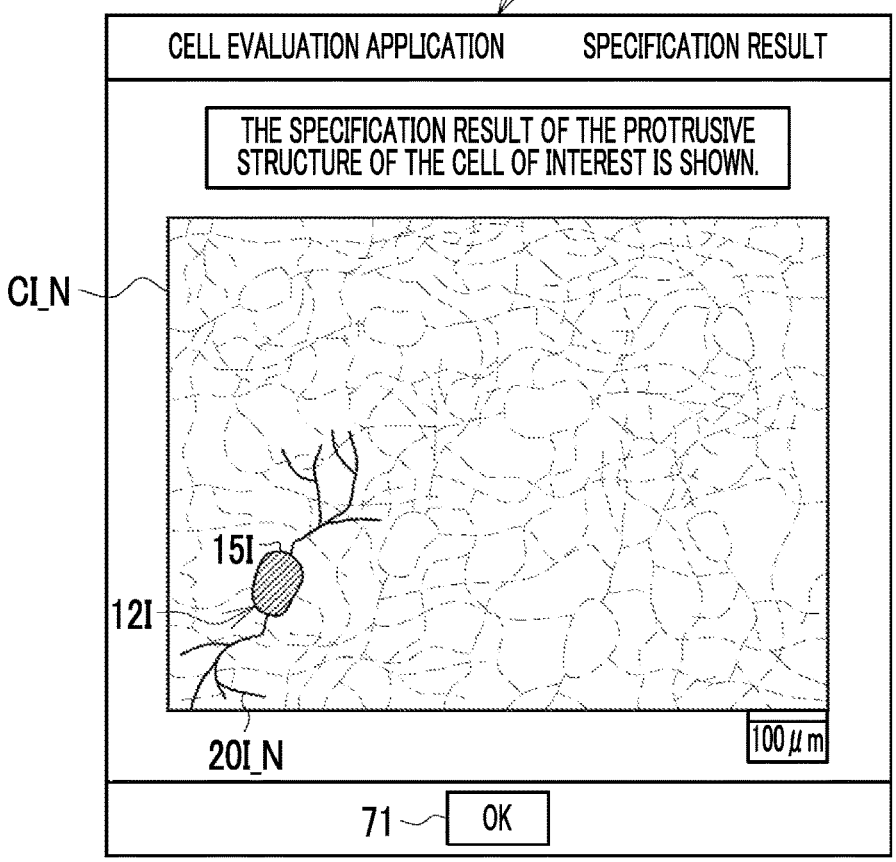
FIG. 14 is a diagram illustrating a specification result display screen.

In FIG. 14, the cell image CI_N on the Nth day of culture, in which the cell body 151 of the cell of interest 12I and the protrusive structure of interest 20I_N are displayed by being colored in red, for example, and the cell of interest 12I and others except for the protrusive structure of interest 20I_N are grayed out as shown by broken lines, is displayed on the specification result display screen 70 that is displayed on the display 34 based on the specification result information SRI under the control of the display control unit 49. That is, the display control unit 49 performs control to display the protrusive structure of interest 20I_N in a display form different from that of other protrusive structures 20 in the cell image CI_N on the Nth day of culture, where the cell image CI_N is an example of the cell image of interest and the latest cell image. In a case where an OK button 71 is selected, the display control unit 49 turns off the display of the specification result display screen 70.

As a method of displaying the protrusive structure of interest 20I_N in a display form different from that of other protrusive structures 20, a method of displaying the contour of the protrusive structure of interest 20I_N with a bold line may be adopted. Further, a method in which a state where the protrusive structure of interest 20I_N is colored and a state where the protrusive structure of interest 20I_N is not colored are alternately repeated at intervals of several seconds may be adopted.

Figure 15:
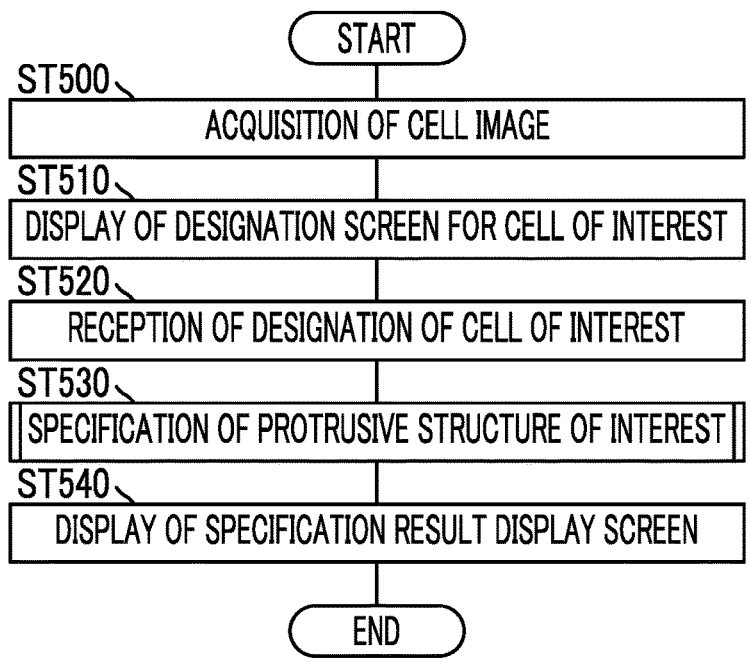
FIG. 15 is a flowchart illustrating a processing procedure of the cell evaluation device.

Next, an operation based on the above configuration will be described with reference to the flowchart of FIG. 15. First, in a case where the operation program 40 is activated in the cell evaluation device 10, as illustrated in FIG. 6, the CPU 32 of the cell evaluation device 10 is allowed to function as the RW control unit 45, the acquisition unit 46, the reception unit 47, the specifying unit 48, and the display control unit 49.

In the cell evaluation device 10, the image set IS is read out from the storage device 30 by the RW control unit 45 and is output to the acquisition unit 46. As a result, the image set IS is acquired by the acquisition unit 46 (a step ST500). The image set IS is output from the acquisition unit 46 to the specifying unit 48. Further, the cell image CI_N on the Nth day of culture in the image set IS is output from the acquisition unit 46 to the display control unit 49. The step ST500 is an example of the "acquisition step" according to the technique of the present disclosure.

As illustrated in FIG. 7, the display control unit 49 displays the designation screen for a cell of interest 60 including the cell image CI_N on the Nth day of culture, on the display 34 (a step ST510). On this designation screen for a cell of interest 60, the operator inputs a marker 61 into the cell body 151 of the cell of interest 12I, and then selects an OK button 62. As a result, the reception unit 47 receives the designation of the cell of interest 12I (a step ST520). The reception unit 47 creates the designation position information SII. The designation position information SII is output from the reception unit 47 to the specifying unit 48. The step ST520 is an example of a "reception step" according to the technique of the present disclosure.

As illustrated in FIG. 8 to FIG. 13, the specifying unit 48 specifies the protrusive structure of interest 20I_N of the cell of interest 12I in the cell image CI_N on the Nth day of culture (a step ST530). The specifying unit 48 creates the specification result information SRI. The specification result information SRI is output from the specifying unit 48 to the display control unit 49. The step ST530 is processing including the step ST100 to the ST170, illustrated in FIG. 8, and is an example of a "specification step" according to the technique of the present disclosure.

As illustrated in FIG. 14, the display control unit 49 displays the specification result display screen 70 on which the protrusive structure of interest 20I_N is displayed in a display form different from that of other protrusive structures 20, on the display 34 (a step ST540). The operator confirms the protrusive structure of interest 20I_N of the cell of interest 12I through the specification result display screen 70 and evaluates the growth state of the cell of interest 12I. The step ST540 is an example of a "display control step" according to the technique of the present disclosure.

As described above, in the cell evaluation device 10, the acquisition unit 46 acquires the image set IS. The reception unit 47 receives the designation of the cell of interest 12I. Then, the specifying unit 48 specifies the protrusive structure of interest 20I_N which extends from the cell of interest 12I. In addition, the display control unit 49 performs control to display of the protrusive structure of interest 20I_N in a display form different from that of other protrusive structures 20 in the cell image CI_N on the Nth day of culture. As a result, it is possible to evaluate the cells of interest 12I individually.

Since the cells of interest 12I can be evaluated individually, it is possible to evaluate not only the growth state but also the position dependence of the growth state. For example, it is possible to compare the growth state between a place where glial cells are dense and a place where glial cells are not dense, between a place where a distance to other nerve cells 12 is close and a place where a distance thereto is far, or the like.

As illustrated in FIG. 8 to FIG. 13, in the specifying unit 48, the difference image DI_K, K+1 of the cell image CI_K on the Kth day and the cell image CI_K+1 on the (K+1)th day is generated. Then, the connectivity between a protrusive structure 20_K, K+1 which is shown in the difference image DI_K, K+1 and a protrusive structure of interest 20I_K which is shown in the cell image CI_K on the Kth day of culture is determined, whereby the protrusive structure of interest 20I_N which is shown in the cell image CI_N on the Nth day of culture is specified. As a result, the protrusive structure of interest 20I_N can be accurately specified. Further, in a case where the method of determining the connectivity is devised as described above, the protrusive structure 20 that is interrupted in some places due to noise can also be specified as the protrusive structure of interest 20I_N.

In the present embodiment, the cell image of interest is the latest cell image in the image set IS. It is conceivable that the protrusive structure 20 in the latest cell image is most complicated in the image set IS. Accordingly, in a case where the protrusive structure of interest 20I in the latest cell image can be revealed, it is possible to further enhance the superiority of the effect that the cells of interest 12I can be evaluated individually.

Second Embodiment

In the second embodiment illustrated in FIG. 16 to FIG. 19, at least any one of the length, the thickness, the area, or the number of branching times of the protrusive structure of interest 20I_N is calculated, and the calculation result is output.

Figure 16:
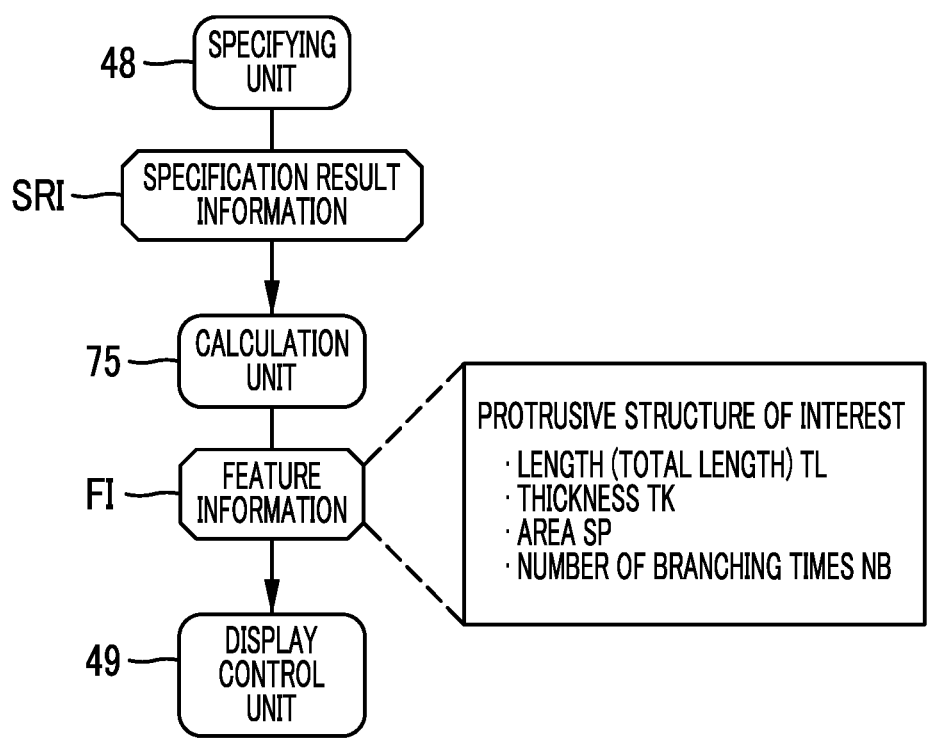
FIG. 16 is a block diagram illustrating a processing unit of a CPU of a cell evaluation device of the second embodiment.

In FIG. 16, the CPU of the cell evaluation device of the second embodiment functions as a calculation unit 75 in addition to each of the processing units 45 to 49 (only the specifying unit 48 and the display control unit 49 are illustrated in FIG. 16) of the first embodiment. The specifying unit 48 outputs the specification result information SRI to the calculation unit 75. The calculation unit 75 calculates the length (the total length) TL, the thickness TK, the area SP, and the number of branching times NB of the protrusive structure of interest 20I_N based on the specification result information SRI. The calculation unit 75 outputs, including the calculation results of each of these index values, a feature information FI representing the features of the protrusive structure of interest 20I_N to the display control unit 49.

Figure 17:
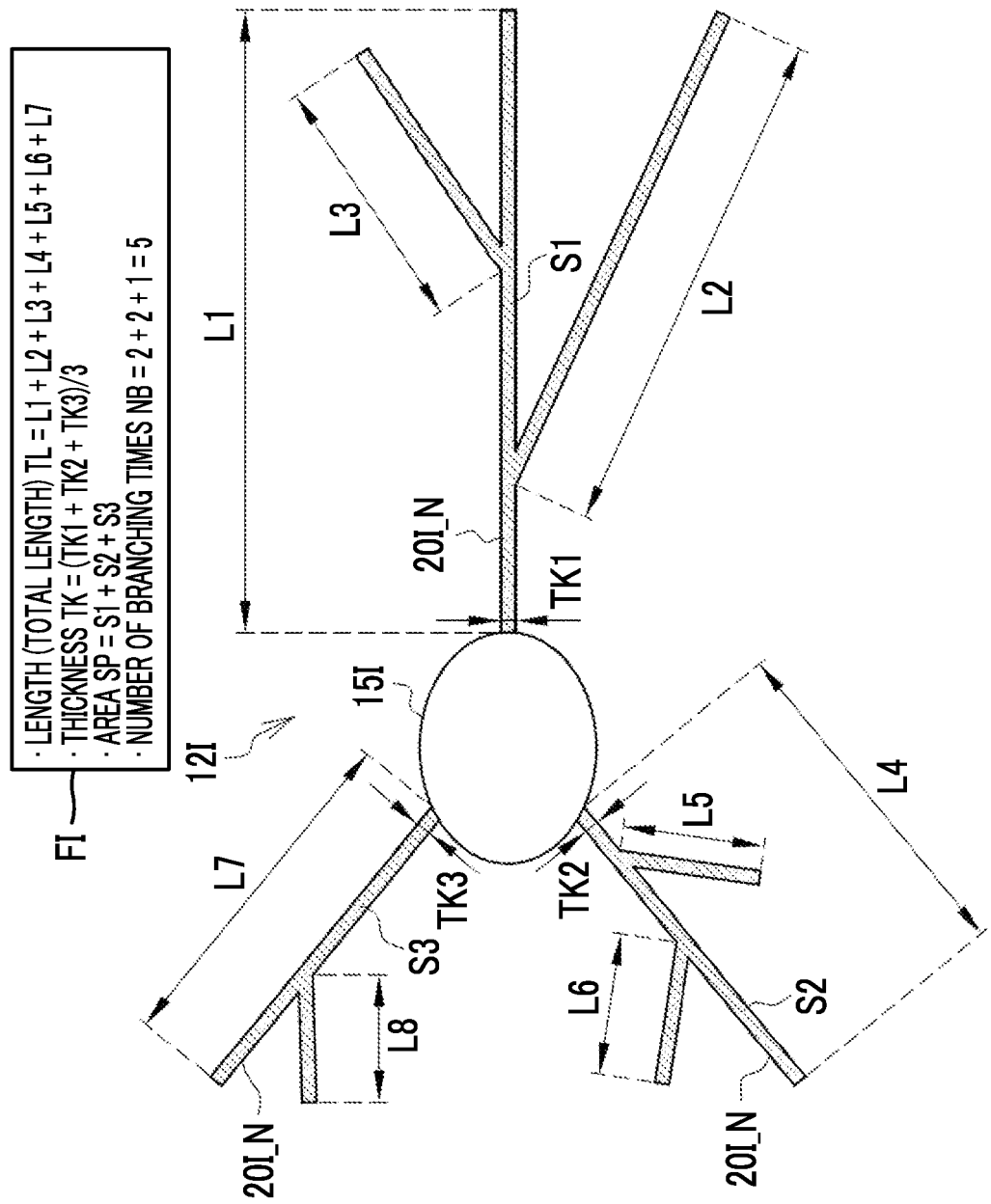
FIG. 17 is a diagram illustrating an example of feature information.
Figure 18:
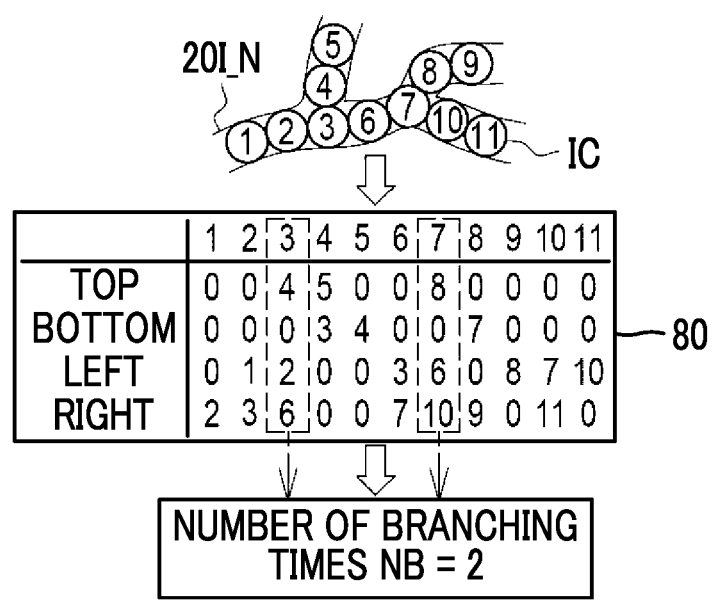
FIG. 18 is a diagram illustrating an outline of a method of determining the number of branching times of the protrusive structure of interest.

As illustrated in FIG. 17, a case where the specifying unit 48 specifies a total of three protrusive structures of interest 20I_N of the cell of interest 12I is conceived. In this case, the length TL of the protrusive structure of interest 20I_N is the sum of the lengths L1, L2, L3, L4, L5, L6, L7, and L8 of the eight protrusions constituting each of the protrusive structures of interest 20I_N. That is, TL=L1+L2+L3+L4+L5+L6+L7+L8. The thickness TK is the average of the thicknesses TK1, TK2, and TK3 at the root (the vicinity of the cell body 15) of each of the protrusive structures of interest 20I_N. That is, TK=(TK1+TK2+TK3)/3.

The area SP is the sum of the areas S1, S2, and S3 of each of the protrusive structures of interest 20I_N. That is, SP=S1+S2+S3. The number of branching times NB is the total number of branching times of each of the protrusive structures of interest 20I_N. That is, NB=2+2+1=5.

The length L of the protrusion is determined, for example, by subjecting the protrusion to the thinning processing and then counting the number of pixels constituting the thinned protrusion. Alternatively, it is determined by adding the diameters of the inscribed circles IC. The area S of each of the protrusive structures of interest 20I_N is determined by counting the number of pixels constituting each of the protrusive structures of interest 20I_N.

The number of branching times NB is determined by using, for example, the technique described in JP2009-063509A. The content of the technique described in JP2009-063509A is to drive a matrix 80 representing the connection relationship of the inscribed circles IC provided in the protrusive structure 20, as outlined in FIG. 18. In the matrix 80, the number of each of the inscribed circles IC of the protrusive structure 20 is arranged in the first row. Then, under the number of each of the inscribed circles IC, the numbers of the inscribed circles IC which are connected to the top, the bottom, the left, and the right, respectively, are arranged. For example, with respect to the inscribed circle IC of number 3, the inscribed circles IC of number 2, number 4, and number 6 are connected to the left, top, and right, respectively, and thus 4, 0 (which means the connection is not present), 2, and 6 are lined up below the number 3. According to such a matrix 80, the number of branching times NB of the protrusive structure of interest 20I_N can be determined. The method of determining the number of branching times NB is not limited to the method described in JP2009-063509A.

Figure 19:
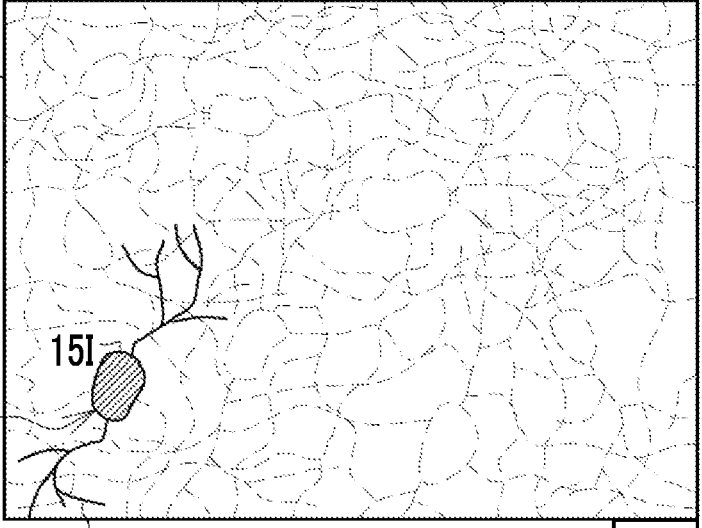
FIG. 19 is a diagram illustrating a specification result display screen of the second embodiment.

The display control unit 49 performs control to display a specification result display screen 85 illustrated in FIG. 19 on the display 34. The specification result display screen 85 is basically the same as the specification result display screen 70 of the first embodiment illustrated in FIG. 14; however, it is different from the specification result display screen 70 in the fact that a display frame 86 of the feature information FI is added. A list of the length TL, the thickness TK, the area SP, and the number of branching times NB of the protrusive structure of interest 20I_N is displayed in the display frame 86. That is, the display control unit 49 is an example of the "output control unit that performs control to output the calculation result of the calculation unit" according to the technique of the present disclosure.

In this manner, in the second embodiment, the calculation unit 75 calculates the length TL, the thickness TK, the area SP, and the number of branching times NB of the protrusive structure of interest 20I_N. Then, the display control unit 49 outputs the calculation result of the calculation unit 75 through the specification result display screen 85. The length TL, the thickness TK, the area SP, and the number of branching times NB of the protrusive structure 20 are important index values for knowing the growth state of the nerve cell 12. Specifically, it can be said that the longer the length TL, the thicker the thickness TK, the larger the area SP, and the larger the number of branching times NB, the better the nerve cell 12 has grown. As a result, the growth state of the cell of interest 12I can be quantitatively evaluated.

The index value calculated by the calculation unit 75 may be at least any one of the length TL, the thickness TK, the area SP, or the number of branching times NB of the protrusive structure of interest 20I_N. Further, as the output form of the calculation result of the calculation unit 75, a form of printing out on a paper medium or a form of outputting as a data file may be adopted instead of or in addition to the specification result display screen 85 of FIG. 19.

Third Embodiment

In the third embodiment illustrated in FIG. 20 to FIG. 23, the number of spines 25 formed on the dendrite 17 is calculated.

Figure 20:
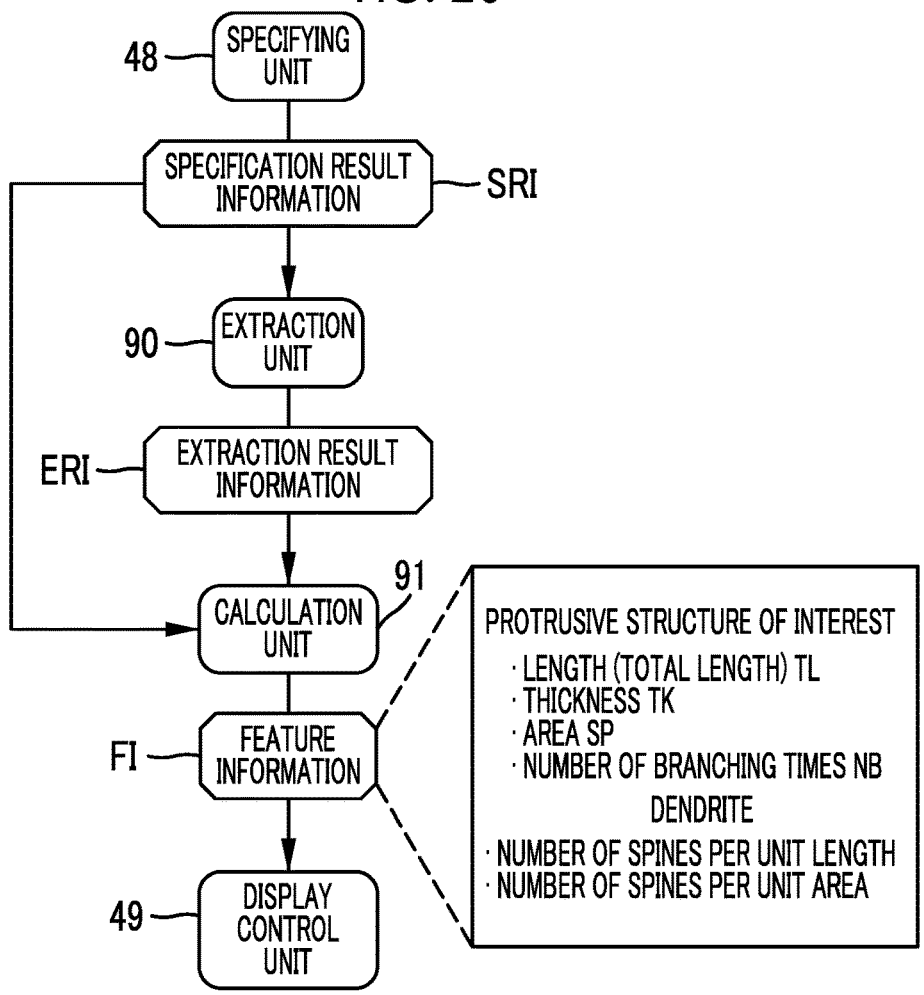
FIG. 20 is a block diagram illustrating a processing unit of a CPU of a cell evaluation device of the third embodiment.

In FIG. 20, the CPU of the cell evaluation device of the third embodiment functions as an extraction unit 90 and a calculation unit 91 in addition to each of the processing units 45 to 49 (only the specifying unit 48 and the display control unit 49 are illustrated in FIG. 20) of the first embodiment. The specifying unit 48 outputs the specification result information SRI to the extraction unit 90 and the calculation unit 91. The extraction unit 90 extracts spines 251 (see FIG. 22) formed on a dendrite 171 (see FIG. 22) in the protrusive structure of interest 20I_N based on the specification result information SRI. The extraction unit 90 outputs an extraction result information ERI representing the extraction result of the spine 251 to the calculation unit 91.

Similarly to the calculation unit 75 of the second embodiment, the calculation unit 91 calculates the length TL, the thickness TK, the area SP, and the number of branching times NB of the protrusive structure of interest 20I_N based on the specification result information SRI. In addition, the calculation unit 91 calculates the number of spines 251 per unit length of the dendrite 171 and the number of spines 251 per unit area of the dendrite 171 based on the extraction result information ERI. The calculation unit 91 outputs the feature information FI to the display control unit 49.

Figure 21:
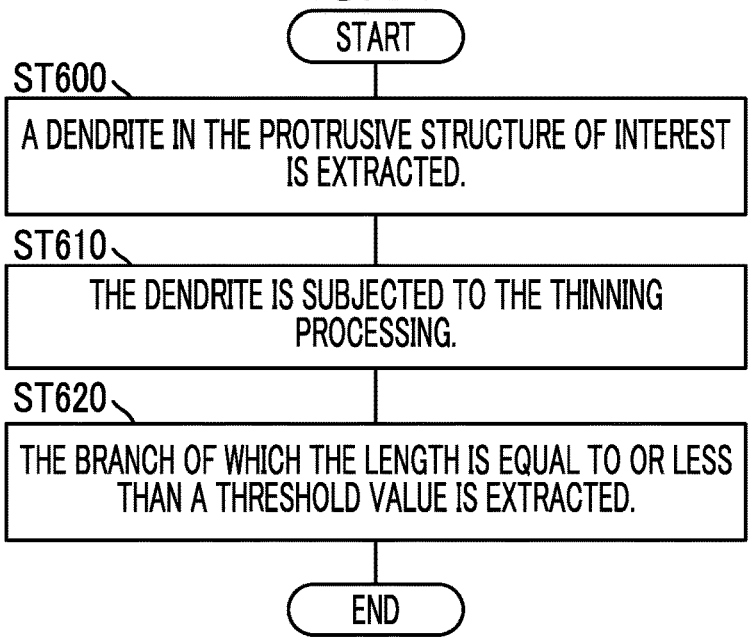
FIG. 21 is a flowchart illustrating a spine extraction procedure.

The extraction of the spine 251 in the extraction unit 90 is carried out, for example, by the procedure illustrated in FIG. 21. First, the extraction unit 90 extracts the dendrite 171 in the protrusive structure of interest 20I_N based on the distance from the cell body 151 to the first branch position (a step ST600). More specifically, the protrusive structure of interest 20I_N located at a position where the distance from the cell body 151 to the first branch position is equal to or lower than a threshold value is extracted as the dendrite 171. This method utilizes the feature that the axon 16 does not form a branch unless it is separated from the cell body 151 by some distance, whereas the dendrite 17 forms a branch in the relatively close vicinity of the cell body 15I.

Figure 22:
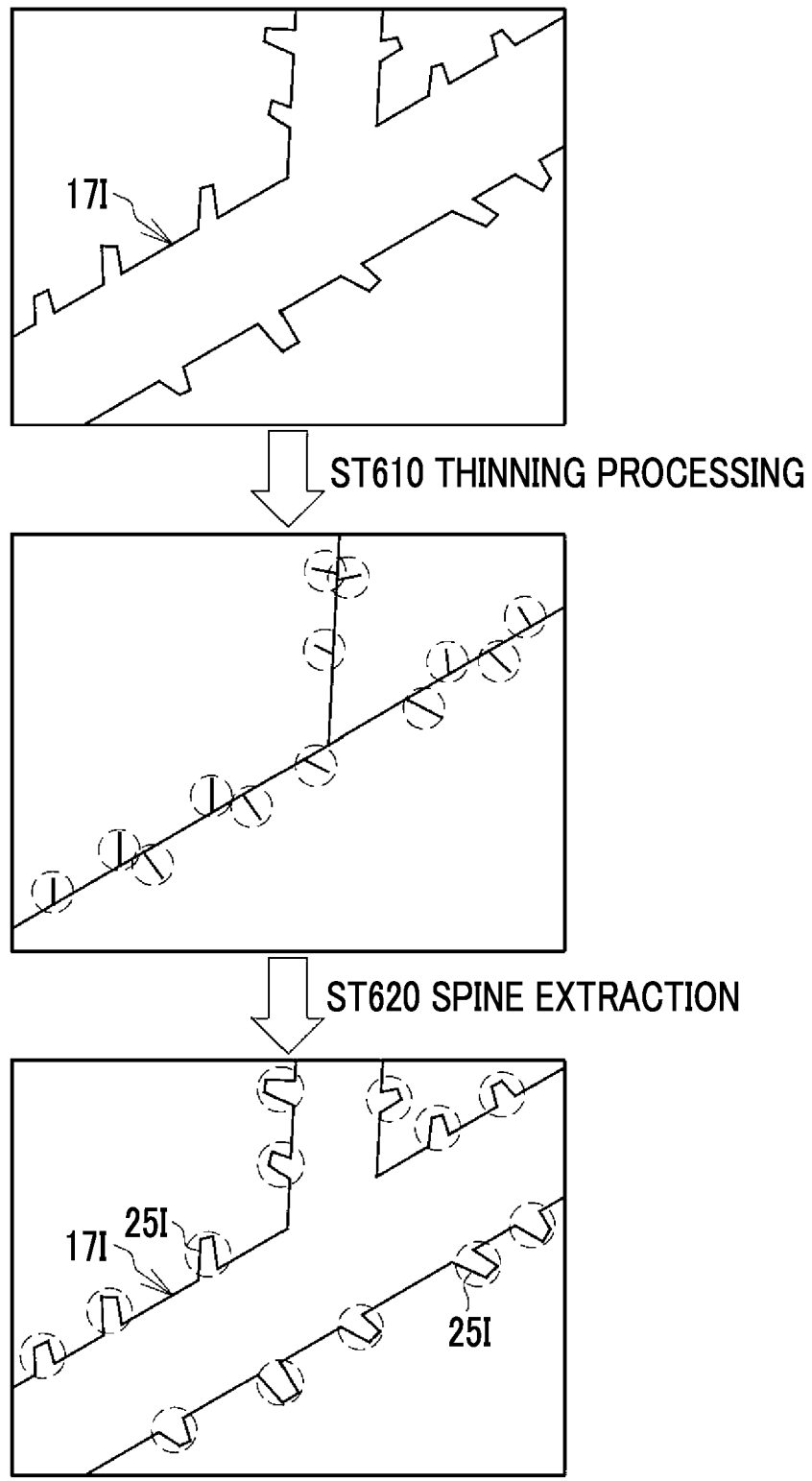
FIG. 22 is a diagram illustrating the spine extraction procedure.

Next, as illustrated in FIG. 22 as well, the extraction unit 90 subjects the dendrite 17I to the thinning processing (a step ST610). Then, the dendrite 17I that has been subjected to the thinning processing is scanned. Among the branches recognized in the scanning process, the extraction unit 90 extracts a branch of which the length is equal to or less than a threshold value as the spine 25I (a step ST620). The threshold value is set to, for example, 3 μm in terms of actual size. The extraction method of the spine 25I is not limited to the method described above.

The calculation unit 91 first calculates the number of spines 25I extracted by the extraction unit 90 based on the extraction result information ERI. Next, the calculation unit 91 recalculates the length and the area of the dendrite 17I from the length TL and the area SP of the protrusive structure of interest 20I_N, which have been calculated based on the specification result information SRI. The calculation unit 91 divides the number of spines 25I by the length of the dendrite 17I to calculate the number of spines 25I per unit length. In addition, the calculation unit 91 divides the number of spines 25I by the area of the dendrite 17I to calculate the number of spines 25I per unit area.

Figure 23:
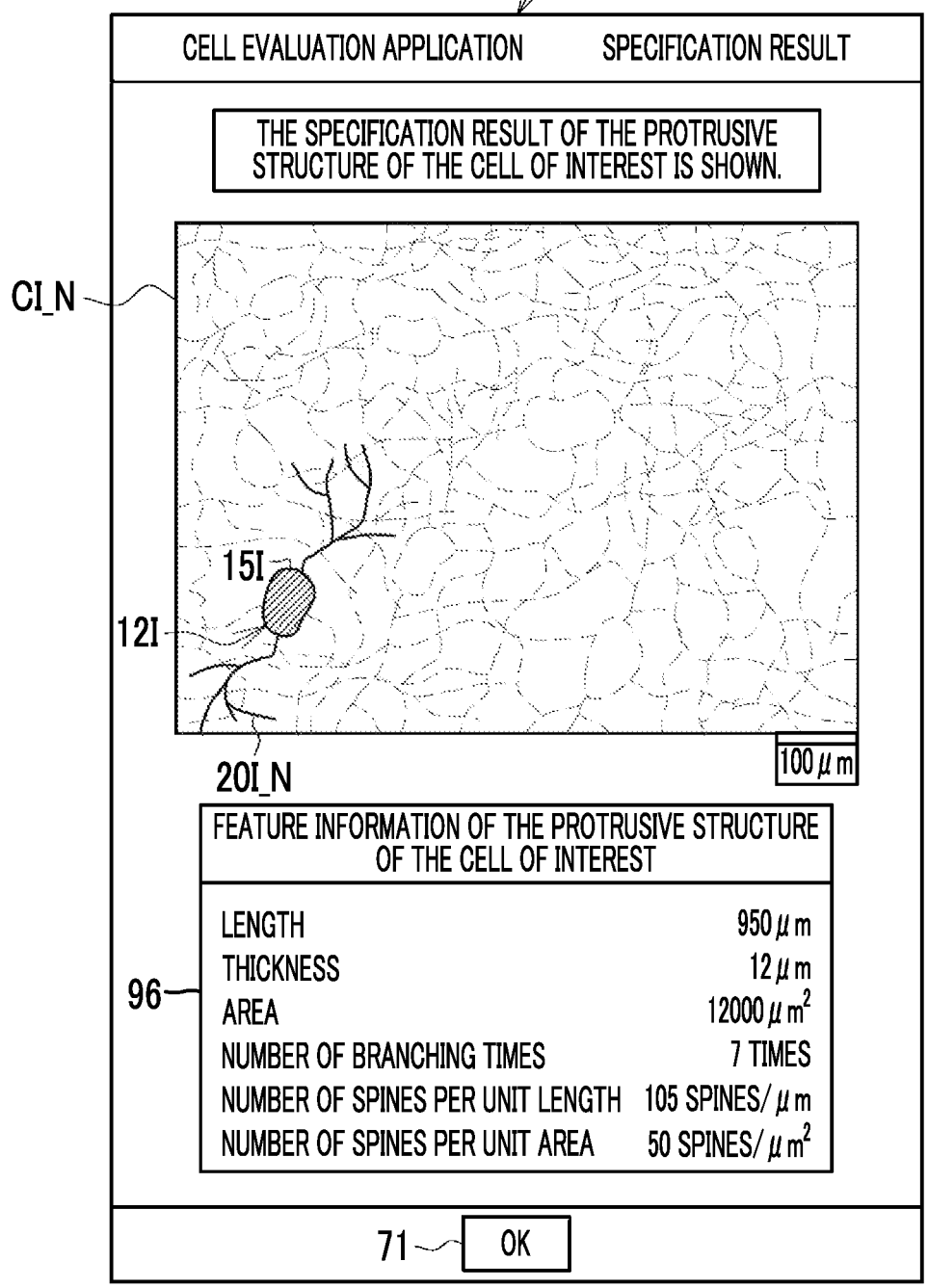
FIG. 23 is a diagram illustrating a specification result display screen of the third embodiment.

The display control unit 49 performs control to display a specification result display screen 95 illustrated in FIG. 23 on the display 34. In terms of the content of the display frame 96, the specification result display screen 95 is different from the specification result display screen 85 of the second embodiment illustrated in FIG. 19. That is, in addition to the length TL, the thickness TK, the area SP, and the number of branching times NB of the protrusive structure of interest 20I_N, a list of the number of spines 25I per unit length of the dendrite 17I and the number of spines 25I per unit area of the dendrite 17I is displayed in the display frame 96.

In this manner, in the third embodiment, the calculation unit 91 calculates the number of spines 25I formed on the dendrite 17I, and further calculates the number of spines 25I per unit length of the dendrite 17I and the number of spines 25I per unit area of the dendrite 17I. Then, the display control unit 49 outputs the calculation result of the calculation unit 91 through the specification result display screen 95. The number of spines 25 per unit length of the dendrite 17 and the number of spines 25 per unit area of the dendrite 17 are also important index values for knowing the growth state of the nerve cells 12. Specifically, it can be said that the larger the number of spines 25 per unit length of the dendrite 17 and the larger the number of spines 25 per unit area of the dendrite 17, the better the nerve cells 12 has grown. As a result, in a case where the number of spines 25I per unit length of the dendrite 17I and the number of spines 25I per unit area of the dendrite 17I are calculated and displayed, the growth state of the cell of interest 12I can be quantitatively evaluated more progressively.

The dendrite 17I in the protrusive structure of interest 20I_N may be extracted by using the fact that the dendrite 17 tends to have a thickness thicker than that of the axon 16. In addition, the dendrite 17I in the protrusive structure of interest 20I_N may be extracted by using the fact that the dendrite 17 tends to have a large thickness in the vicinity of the cell body 15 and tend to become thinner as the dendrite 17 becomes separated from the cell body 15.

The index value to be calculated by the calculation unit 91 may be at least any one of the number of spines 25I per unit length of the dendrite 17I or the number of spines 25I per unit area of the dendrite 17I. Further, as the output form of the calculation result of the calculation unit 91, similarly to the second embodiment, a form of printing out on a paper medium or a form of outputting as a data file may be adopted instead of or in addition to the specification result display screen 95 of FIG. 23.

The method of extracting the dendrite 17I in the protrusive structure of interest 20I_N, which is represented in the step ST600 of FIG. 21, may be applied to the first embodiment. In this case, the display control unit 49 performs control to display the axon (not illustrated in the drawing) and the dendrite 17I of the protrusive structure of interest 20I_N in different display forms on the specification result display screen 70 illustrated in FIG. 14.

In addition, the method of extracting the dendrite 17I in the protrusive structure of interest 20I_N, which is represented in the step ST600 of FIG. 21, may be applied to the second embodiment. In this case, the calculation unit 75 calculates the length TL, the thickness TK, the area SP, and the number of branching times NB of the axon of the protrusive structure of interest 20I_N, and separately the length TL, thickness TK, the area SP, and the number of branching times NB of the dendrite 17I. The display control unit 49 performs control to display separately displaying a list of the length TL, the thickness TK, the area SP, and the number of branching times NB of the axon of the protrusive structure of interest of 20I_N, and a list of the length TL, the thickness TK, the area SP, and the number of branching times NB of the dendrite 17I in the display frame 86, on the specification result display screen 85 illustrated in FIG. 19.

Fourth Embodiment

Figure 24:
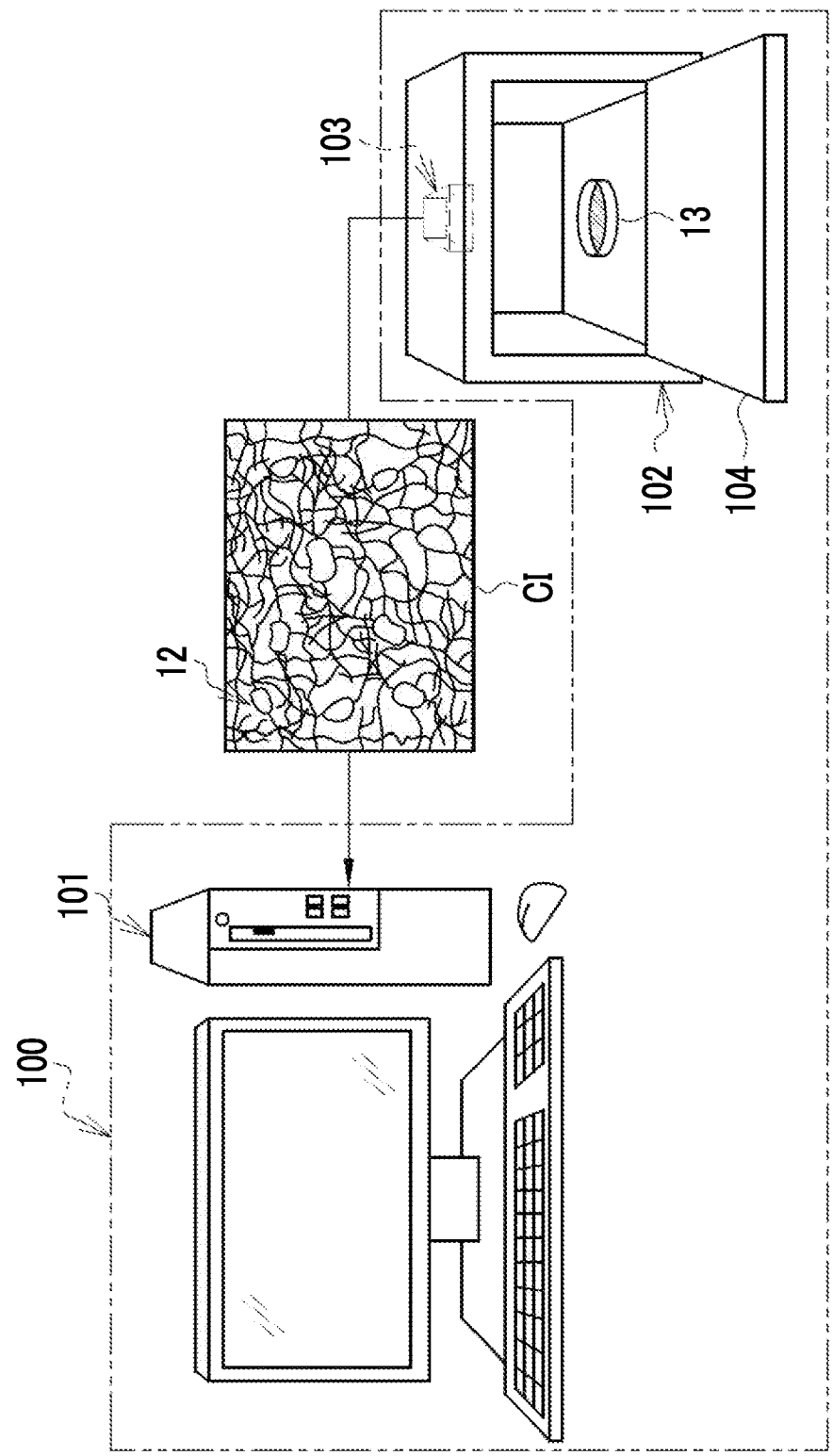
FIG. 24 is a diagram illustrating a cell culture system of the fourth embodiment.

In the fourth embodiment illustrated in FIG. 24, a cell culture system 100 is used.

In FIG. 24, the cell culture system 100 includes a cell evaluation device 101, an incubator 102, and an imaging device 103. The cell evaluation device 101 is any of the cell evaluation devices which are respectively described in each of the above embodiments. The incubator 102 accommodates the culture instrument 13. The incubator 102 has a function of keeping the temperature in the tank at a constant value suitable for culturing nerve cells 12. In addition, the incubator 102 has a function of supplying a medium or the like to the culture instrument 13. For this reason, after accommodating the culture instrument 13 in the incubator 102, it is possible to complete the culture without taking out the culture instrument 13 even once. It is noted that FIG. 24 shows a state where a cover 104 of the incubator 102 is opened and the culture instrument 13 is placed on the bottom surface. During culture, the cover 104 is closed.

The imaging device 103 is built on the upper surface which faces the bottom surface of the incubator 102, on which the culture instrument 13 is placed. The imaging device 103 takes the cell image CI in a state where the culture instrument 13 is accommodated in the incubator 102. The imaging device 103 takes the cell image CI at preset regular imaging intervals, for example, every day. The imaging device 103 transmits the taken cell image CI to the cell evaluation device 101. The cell evaluation device 101 receives the cell image CI from the imaging device 103 and stores the received cell image CI in a storage device (not illustrated in the drawing).

As described above, in the fourth embodiment, the cell culture system 100 includes the cell evaluation device 101, the incubator 102, and the imaging device 103 is used. The imaging device 103 takes the cell image CI in a state where the culture instrument 13 is accommodated in the incubator 102. As a result, as illustrated in FIG. 3 of the first embodiment, the operator can save the labor of taking the cell image CI by using the imaging device 11. Further, the operator does not have to worry about setting the culture instrument 13 in the imaging device 11 so that the imaging position is the same every time.

In addition, the cell image CI may be taken with the imaging device 103 at relatively short imaging intervals, for example, at every hour. Then, the plurality of cell images CI obtained as described above are analyzed, and the cell image CI taken at the timing at which the individual protrusive structures 20 extending from the cell bodies 15 of the individual nerve cells 12 extend and join first time are extracted. This extracted cell image CI or the cell image CI taken at the timing immediately before the extracted cell image CI is set as the oldest image of the image set IS.

In addition, the imaging intervals of the cell image CI taken by the imaging device 103 may be set to be equal to or less than the difference between the time point at which the individual protrusive structures 20 extending from the cell bodies 15 of the individual nerve cells 12 extend and join first time and the time point at which they join next time.

The timing at which the nerve cell 12 is evaluated in the cell evaluation device is not limited to the timing after the end of the culture period illustrated in FIG. 3. The evaluation may be carried out in the middle of the culture period. The cell image of interest in this case is no longer the cell image CI_N on the Nth day of culture. In addition, for example, on the fifth day of culture, the nerve cell 12 may be evaluated using the cell image CI_3 on the third day of culture as the cell image of interest. Alternatively, after the end of the culture period, the nerve cells 12 may be evaluated using the cell image CI_1 on the first day of culture and the cell image CI other than the cell image CI_N on the Nth day of culture as the cell image of interest. In other words, the cell image of interest may be any cell image as long as it is not the oldest cell image CI in the image set IS.

A plurality of cells of interest 12I may be designated at one time. In this case, the specifying unit 48 specifies the protrusive structure of interest 20I_N for every individual cell of interest 12I. In addition, the display control unit 49 performs control to display the protrusive structure of interest 20I_N of each of the cells of interest 12I in a different display form on the specification result display screen. Alternatively, the display control unit 49 controls switching of the highlight display of the protrusive structure of interest 20I_N for every cell of interest 12I.

In each of the above embodiments, the nerve cell 12 is exemplified as the cell to be evaluated; however, the present invention is not limited thereto. Any cell having a protrusive structure may be used, and for example, a microglia (also referred to as a microglial cell) or an astrocyte (also referred to as an astroglia or a macroglia) may be used. Alternatively, it may be a dendritic cell such as a veil cell or a Langerhans cell.

Various modifications may be made to the hardware configuration of the computer that constitutes the cell evaluation device. For example, the cell evaluation device may be composed of a plurality of computers separated as hardware for the purpose of improving processing capacity and reliability. Specifically, the functions of the RW control unit 45 and the acquisition unit 46 and the functions of the reception unit 47, the specifying unit 48, and the display control unit 49 are distributed to two computers. In this case, the cell evaluation device is composed of two computers.

In this manner, the hardware configuration of the computer of the cell evaluation device may be appropriately modified according to necessary performance such as processing capacity, security, and reliability. Further, as well as the hardware, the application program such as the operation program 40 may be duplicated or stored in a plurality of storage devices in a distributed manner for the purpose of ensuring security and reliability.

In each of the above embodiments, for example, as a hardware structure of processing units that execute various processing, such as the RW control unit 45, the acquisition unit 46, the reception unit 47, the specifying unit 48, the display control unit 49, the calculation units 75 and 91, and the extraction unit 90, the various processors described below may be used. As described above, in addition to the CPU 32 that is a general-purpose processor that executes software (operation program 40) to function as various processing units, various processors include a programmable logic device (PLD) that is a processor of which a circuit configuration is changeable after manufacturing, such as a field programmable gate array (FPGA), a dedicated electrical circuit that is a processor having a circuit configuration specifically designed to execute a specific process, such as an application specific integrated circuit (ASIC), or the like.

One processing unit may be composed of one of these various processors or may be composed of a combination of two or more processors of the same type or different types (for example, a combination of a plurality of FPGAs and/or a combination of a CPU and an FPGA). Further, a plurality of processing units may be composed of one processor.

As an example in which the plurality of processing units is composed of one processor, first, as represented by a computer such as a client and a server, there is a configuration in which one processor is composed of a combination of one or more CPUs and software and the processor functions as a plurality of processing units. Secondly, as represented by a system on chip (SoC) or the like, there is a configuration in which a processor that realizes the functions of the entire system including a plurality of processing units by one integrated circuit (IC) chip is used. As described above, one or more of the above various processors are used to constitute the hardware structure of the various processing units.

Further, as a hardware structure of these various processors, more specifically, an electrical circuit (circuitry) in which circuit elements such as semiconductor elements are combined may be used.

From the above description, the disclosure described in Supplementary note 1 below can be understood.

[Supplementary Note 1]

A cell evaluation device comprising:

an acquisition processor that acquires an image set of a plurality of cell images in which a plurality of cells having a protrusive structure are imaged in time series during culture;

a reception processor that receives a designation of a cell of interest which is a cell of interest to a user, the cell being at least one cell among the plurality of cells which are shown in one cell image of interest other than an oldest cell image in the image set;

a specification processor that captures a growth process of the protrusive structure based on the image set to specify a protrusive structure of interest, which is the protrusive structure extending from the cell of interest in the cell image of interest; and a display control processor that performs control to display the protrusive structure of interest in a display form different from that of other protrusive structures in the cell image of interest.

The technique of the present disclosure may be appropriately combined with the above-described various embodiments and various modifications. In addition, it is needless to say that various configurations may be adopted within a scope without departing from the concept of the present disclosure and are not limited to each of the above embodiments. Further, the technique of the present disclosure extends to a storage medium that stores the program in a non-temporary manner, in addition to the program.

The above-described content and the above-illustrated content are detailed descriptions of portions related to the technique of the present disclosure, which are merely an example of the technique of the present disclosure. For example, the description of the above configurations, functions, operations, and effects is an example of the description of configurations, functions, operations, and effects of portions related to the technique of the present disclosure. Accordingly, within the scope without departing from the concept of the technique of the present disclosure, unnecessary portions may be removed, new elements may be added or replaced for the above-described content and the above-illustrated content. In addition, in order to avoid complication and facilitate understanding of the portions related to the technique of the present disclosure, in the above-described content and the above-illustrated content, the description of the common technical knowledge or the like that does not need special explanation in implementing the technique of the present disclosure is omitted.

In the present specification, "A and/or B" is synonymous with "at least one of A or B". That is, "A and/or B" may refer to only A, only B, or a combination of A and B. In addition, in the present specification, the same concept as "A and/or B" is also applied to a case where three or more matters are linked by "and/or".

All documents, patent applications, and technical standards disclosed in this specification are incorporated in this specification by reference in such a manner that the incorporation by reference of the individual document, patent application, and technical standard are handled to the same extent as in the specific and individual description thereof

What is claimed is:

1. A cell evaluation device comprising:
a memory;
a display; and
a processor coupled to the memory and the display, the processor being configured to:
acquire an image set of a plurality of cell images in which a plurality of cells having a protrusive structure are imaged in time series during culture;
receive a designation of a cell of interest which is a cell of interest to a user, the cell being at least one cell among the plurality of cells which are shown in one cell image of interest other than an oldest cell image in the image set;
capture a growth process of the protrusive structure based on the image set to specify a protrusive structure of interest, which is the protrusive structure extending from the cell of interest in the cell image of interest; and
display, at the display, the cell of interest and the protrusive structure of interest in a display form different from that of other cells and protrusive structures in the cell image.

2. The cell evaluation device according to claim 1, wherein the processor is configured to:
generate a difference image of two cell images which are chronologically continuous in the image set, and
determine a connectivity between the protrusive structure which is shown in the difference image and the protrusive structure which is shown in an older cell image of the two cell images which are chronologically continuous to specify the protrusive structure of interest.

3. The cell evaluation device according to claim 1, wherein the processor is further configured to:
calculate at least any one of a length, a thickness, an area, or the number of branching times of the protrusive structure of interest, and
output a calculation result.

4. The cell evaluation device according to claim 3, wherein the cell is a nerve cell, the protrusive structure is a dendrite, and
the processor is further configured to configure the number of spines formed on the dendrite.

5. The cell evaluation device according to claim 4, wherein the processor is configured to:
calculate at least one of the number of the spines per unit length of the dendrite or the number of the spines per unit area of the dendrite.

6. The cell evaluation device according to claim 1, wherein the cell image of interest is a latest cell image in the image set.

7. An operation method for a cell evaluation device, comprising:
an acquisition step of acquiring an image set of a plurality of cell images in which a plurality of cells having a protrusive structure are imaged in time series during culture;
a reception step of receiving a designation of a cell of interest which is a cell of interest to a user, the cell being at least one cell among the plurality of cells which are shown in one cell image of interest other than an oldest cell image in the image set;
a specification step of capturing a growth process of the protrusive structure based on the image set to specify a protrusive structure of interest, which is the protrusive structure extending from the cell of interest in the cell image of interest; and
a display control step of performing control to display the cell of interest and the protrusive structure of interest in a display form different from that of other cells and protrusive structures in the cell image.

8. A non-transitory computer-readable storage medium storing an operation program causing a computer to execute a process for a cell evaluation device, the process comprising:
acquiring an image set of a plurality of cell images in which a plurality of cells having a protrusive structure are imaged in time series during culture,
receiving a designation of a cell of interest which is a cell of interest to a user, the cell being at least one cell among the plurality of cells which are shown in one cell image of interest other than an oldest cell image in the image set,
capturing a growth process of the protrusive structure based on the image set to specify a protrusive structure of interest, which is the protrusive structure extending from the cell of interest in the cell image of interest, and
displaying the cell of interest and the protrusive structure of interest in a display form different from that of other cells and protrusive structures in the cell image.

9. A cell culture system comprising:
the cell evaluation device according to claim 1;
an incubator that accommodates a culture instrument of the cell; and
an imaging device that takes an image of the cell in a state where the culture instrument is accommodated in the incubator.

* * * * *